US012148156B2

(12) United States Patent
Taki

(10) Patent No.: US 12,148,156 B2
(45) Date of Patent: Nov. 19, 2024

(54) ESTIMATION DEVICE, ESTIMATION METHOD, AND ESTIMATION PROGRAM

(71) Applicant: FUJIFILM Corporation, Tokyo (JP)

(72) Inventor: Tomoko Taki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 450 days.

(21) Appl. No.: 17/717,215

(22) Filed: Apr. 11, 2022

(65) Prior Publication Data
US 2022/0335605 A1 Oct. 20, 2022

(30) Foreign Application Priority Data
Apr. 14, 2021 (JP) .................. 2021-068641

(51) Int. Cl.
*G06T 7/00* (2017.01)
*A61B 6/00* (2024.01)
(Continued)

(52) U.S. Cl.
CPC ............ *G06T 7/0012* (2013.01); *A61B 6/032* (2013.01); *A61B 6/505* (2013.01); *A61B 6/5235* (2013.01);
(Continued)

(58) Field of Classification Search
CPC ......... G06T 7/0012; G06T 2207/10081; G06T 2207/20084; G06T 2207/20081;
(Continued)

(56) References Cited

U.S. PATENT DOCUMENTS 6,064,716 A 5/2000 Siffert et al.
2004/0264628 A1* 12/2004 Besson .................. G21K 1/10
378/5

(Continued)

FOREIGN PATENT DOCUMENTS

JP H09-108206 A 4/1997
JP 2006-271437 A 10/2006
(Continued)

OTHER PUBLICATIONS

Notification of Submission of Publications by a third party; mailed by the Japanese Patent Office on Oct. 31, 2023, which corresponds to Japanese Patent Application No. 2021-068641 and is related to U.S. Appl. No. 17/717,215; with English translation.
(Continued)

*Primary Examiner* — Allen H Nguyen
(74) *Attorney, Agent, or Firm* — Studebaker & Brackett PC

(57) ABSTRACT

At least one processor is provided, in which the processor functions as a trained neural network that derives an estimation result relating to a composition of a soft tissue of a subject from a simple radiation image acquired by simply imaging the subject, or a DXA scanning image acquired by imaging the subject by a DXA method. The trained neural network learns using, as teacher data, two radiation images acquired by imaging the subject with radiation having different energy distributions, the radiation image of the subject and a soft part image representing the soft tissue of the subject, or a composite two-dimensional image representing the subject derived by combining a three-dimensional CT image of the subject, and information relating to the composition of the soft tissue of the subject.

18 Claims, 19 Drawing Sheets

(51) Int. Cl.
*A61B 6/03* (2006.01)
*A61B 6/50* (2024.01)

(52) U.S. Cl.
CPC ........... *G06T 2207/10081* (2013.01); *G06T 2207/10116* (2013.01); *G06T 2207/20081* (2013.01); *G06T 2207/20084* (2013.01)

(58) Field of Classification Search
CPC .......... G06T 2207/10116; A61B 6/032; A61B 6/505; A61B 6/5235
USPC ......................................................... 382/131
See application file for complete search history.

(56) References Cited

U.S. PATENT DOCUMENTS

| | | | |
|---|---|---|---|
| 2007/0276270 A1* | 11/2007 | Tran | A61B 5/0022 600/508 |
| 2011/0305405 A1 | 12/2011 | Kawamura | |
| 2018/0122094 A1 | 5/2018 | Naito | |
| 2019/0102877 A1 | 4/2019 | Payne et al. | |
| 2020/0082525 A1* | 3/2020 | Xu | A61B 5/02042 |
| 2020/0160509 A1* | 5/2020 | Pack | G16H 30/40 |
| 2022/0051398 A1* | 2/2022 | Watanabe | A61B 6/505 |

FOREIGN PATENT DOCUMENTS

| | | |
|---|---|---|
| JP | 2011-255060 A | 12/2011 |
| JP | 2015-043959 A | 3/2015 |
| JP | 2019-063499 A | 4/2019 |
| WO | 2019/208037 A1 | 10/2019 |
| WO | 2020/054738 A1 | 3/2020 |

OTHER PUBLICATIONS

Naoki Nakanishi et al.; "Preliminary investigation on decomposition of individual muscles and bones of lower extremity from single radiograph using CycleGAN", IEICE Technical Report, vol. 119, No. 193, Aug. 28, 2019, pp. 1-6.

* cited by examiner

ESTIMATION DEVICE, ESTIMATION METHOD, AND ESTIMATION PROGRAM

CROSS REFERENCE TO RELATED APPLICATIONS

The present application claims priority under 35 U.S.C. § 119 to Japanese Patent Application No. 2021-068641 filed on Apr. 14, 2021. The above application is hereby expressly incorporated by reference, in its entirety, into the present application.

BACKGROUND

Technical Field

The present disclosure relates to an estimation device, an estimation method, and an estimation program.

Related Art

A dual x-ray absorptiometry (DXA) method is known as one of typical bone mineral quantification methods used for diagnosing a bone mineral density in a bone disease, such as osteoporosis. The DXA method is a method for calculating bone mineral density from a pixel value of a radiation image obtained by performing imaging by the radiation of two types of energies by using radiation incident on and transmitted through a human body, which is attenuated by a mass attenuation coefficient $\mu$ ($cm^2/g$), density $\rho$ ($g/cm^3$) and a thickness t (cm), which depend on a substance (for example, a bone) that configures the human body.

In addition, the technology of deriving a ratio of each of a fat tissue and a lean tissue of each pixel in a DXA image is known (see JP2019-63499A). The technology disclosed in JP2019-63499A measures a fat tissue ratio and a lean tissue (muscle, non-fat, and non-mineral tissue) ratio by analyzing a combination of low-energy and high-energy DXA images.

In addition, various methods for evaluating the bone mineral density using a radiation image acquired by imaging a subject have been proposed. For example, U.S. Pat. No. 6,064,716A and WO2020/054738A propose a method for estimating information relating to the bone mineral density from an image in which the bone appears by using a trained neural network constructed by subjecting a neural network to learning. In the method disclosed in U.S. Pat. No. 6,064,716A, the neural network learns using the image in which the bone appears acquired by simple imaging and the bone mineral density as teacher data. In addition, in the method disclosed in WO2020/054738A, the neural network learns using the image in which the bone appears acquired by the simple imaging, the bone mineral density, and the information relating to the bone mineral density (for example, age, gender, weight, drinking habit, smoking habit, fracture history, body fat percentage, and subcutaneous fat percentage) as the teacher data.

Note that the simple imaging is an imaging method for acquiring one two-dimensional image, which is a transmission image of the subject, by emitting the radiation to the subject once. In the following description, the radiation image acquired by simple imaging will be referred to as a simple radiation image.

On the other hand, it is desired to estimate a composition of a soft tissue such as muscle and fat of a subject with high accuracy.

SUMMARY OF THE INVENTION

The present disclosure has been made in view of the above circumstances, and is to enable estimation of a composition of a soft tissue of a subject with high accuracy.

The present disclosure relates to an estimation device comprising at least one processor, in which the processor functions as a trained neural network that derives an estimation result relating to a composition of a soft tissue of a subject from a simple radiation image acquired by simply imaging the subject, or a DXA scanning image acquired by imaging the subject by a DXA method, and the trained neural network learns using, as teacher data, (i) two radiation images acquired by imaging the subject with radiation having different energy distributions, (ii) the radiation image of the subject and a soft part image representing the soft tissue of the subject, or (iii) a composite two-dimensional image representing the subject derived by combining a three-dimensional CT image of the subject, and information relating to the composition of the soft tissue of the subject.

Note that the estimation device according to the present disclosure, the information relating to the composition of the soft tissue may be derived based on a pixel value of a soft region of a soft part image derived from the two radiation images acquired by imaging the subject with the radiation having different energy distributions.

In addition, the estimation device according to the present disclosure, the information relating to the composition of the soft tissue may be obtained by specifying a soft region in the CT image, deriving an attenuation coefficient of radiation in the soft region, and deriving the information relating to the composition of the soft tissue based on a density of the composition of the soft tissue, which is derived based on the attenuation coefficient of the radiation and a mass attenuation coefficient in the soft region.

In addition, the estimation device according to the present disclosure, the information relating to the composition of the soft tissue may be derived by projecting the density of the composition at each position in the soft region in a predetermined direction.

In addition, the estimation device according to the present disclosure, the information relating to the composition of the soft tissue may include at least one of a muscle mass per unit area, a muscle mass per unit volume, a fat mass per unit area, a fat mass per unit volume, disease information representing an affection risk of a predetermined disease or a disease level of the predetermined disease, or a falling-down rate.

In addition, the estimation device according to the present disclosure, the disease information may be derived by deriving the muscle mass of a predetermined part of the subject, and specifying the disease information based on correspondence relationship information representing a correspondence relationship between the disease information representing the affection risk of the predetermined disease or the disease level of the predetermined disease and the muscle mass of the predetermined part, and the muscle mass.

In addition, the estimation device according to the present disclosure, the disease information may be derived by deriving the muscle mass and a bone mineral density of a predetermined part of the subject, and specifying the disease information based on correspondence relationship information representing a correspondence relationship between the disease information representing the affection risk of the predetermined disease or the disease level of the predetermined disease and the muscle mass of the predetermined part, the muscle mass, and the bone mineral density.

In addition, the estimation device according to the present disclosure, the predetermined part may be a lower limb, the predetermined disease may be diabetes, and the disease information may be the affection risk of the diabetes.

In addition, the estimation device according to the present disclosure, the predetermined part may be limbs or a whole body, the predetermined disease may be sarcopenia, and the disease information may be the disease level of the sarcopenia.

In addition, the estimation device according to the present disclosure, the falling-down rate may be derived by deriving the muscle mass of a predetermined part of the subject, and specifying the falling-down rate based on correspondence relationship information representing a correspondence relationship between muscle information, which is the muscle mass of the predetermined part or a muscle strength in accordance with the muscle mass of the predetermined part, and the falling-down rate of the subject, and the muscle mass.

In addition, the estimation device according to the present disclosure, the falling-down rate may be derived by deriving the muscle mass and a bone mineral density of a predetermined part of the subject, and specifying the falling-down rate based on correspondence relationship information representing a correspondence relationship between muscle information, which is the muscle mass of the predetermined part or a muscle strength in accordance with the muscle mass of the predetermined part, and the falling-down rate of the subject, the muscle mass, and the bone mineral density.

In addition, the estimation device according to the present disclosure, the predetermined part may be at least one of a lower limb or a buttock.

In addition, the estimation device according to the present disclosure, the processor may function as the trained neural network that derives the estimation result relating to the composition of the soft tissue from the DXA scanning image, and the trained neural network may learn using, as the teacher data, a low-resolution composite two-dimensional image obtained by performing processing of reducing a resolution on the composite two-dimensional image, and the information relating to the composition of the soft tissue of the subject.

In addition, the estimation device according to the present disclosure, the low-resolution composite two-dimensional image may be an image in which an average value of pixel values of a plurality of adjacent pixels of the composite two-dimensional image is used as the pixel values of the plurality of adjacent pixels, and sizes of the plurality of adjacent pixels may correspond to one pixel size of the DXA scanning image.

In addition, the estimation device according to the present disclosure, the low-resolution composite two-dimensional image may be an image obtained by performing movement average processing on the composite two-dimensional image in one direction, and the one direction may correspond to a scanning direction of the DXA scanning image.

In addition, the estimation device according to the present disclosure, the low-resolution composite two-dimensional image may be an image generated by generating a first low-resolution image in which an average value of pixel values of a plurality of adjacent pixels of the composite two-dimensional image is used as the pixel values of the plurality of adjacent pixels, and performing movement average processing on the first low-resolution image in one direction, sizes of the plurality of adjacent pixels may correspond to one pixel size of the DXA scanning image, and the one direction may correspond to a scanning direction of the DXA scanning image.

The present disclosure relates to an estimation method comprising using a trained neural network that derives an estimation result relating to a composition of a soft tissue of a subject from a simple radiation image acquired by simply imaging the subject, or a DXA scanning image acquired by imaging the subject by a DXA method to derive the estimation result relating to the composition of the soft tissue from the simple radiation image or the DXA scanning image, in which the trained neural network learns using, as teacher data, (i) two radiation images acquired by imaging the subject with radiation having different energy distributions, (ii) the radiation image of the subject and a soft part image representing the soft tissue of the subject, or (iii) a composite two-dimensional image representing the subject derived by combining a three-dimensional CT image of the subject, and information relating to the composition of the soft tissue of the subject.

Note that the estimation method according to the present disclosure may be provided as a program executed by a computer.

According to the present disclosure, it is possible to estimate the composition of the soft tissue of the subject with high accuracy.

DETAILED DESCRIPTION

Figure 1:
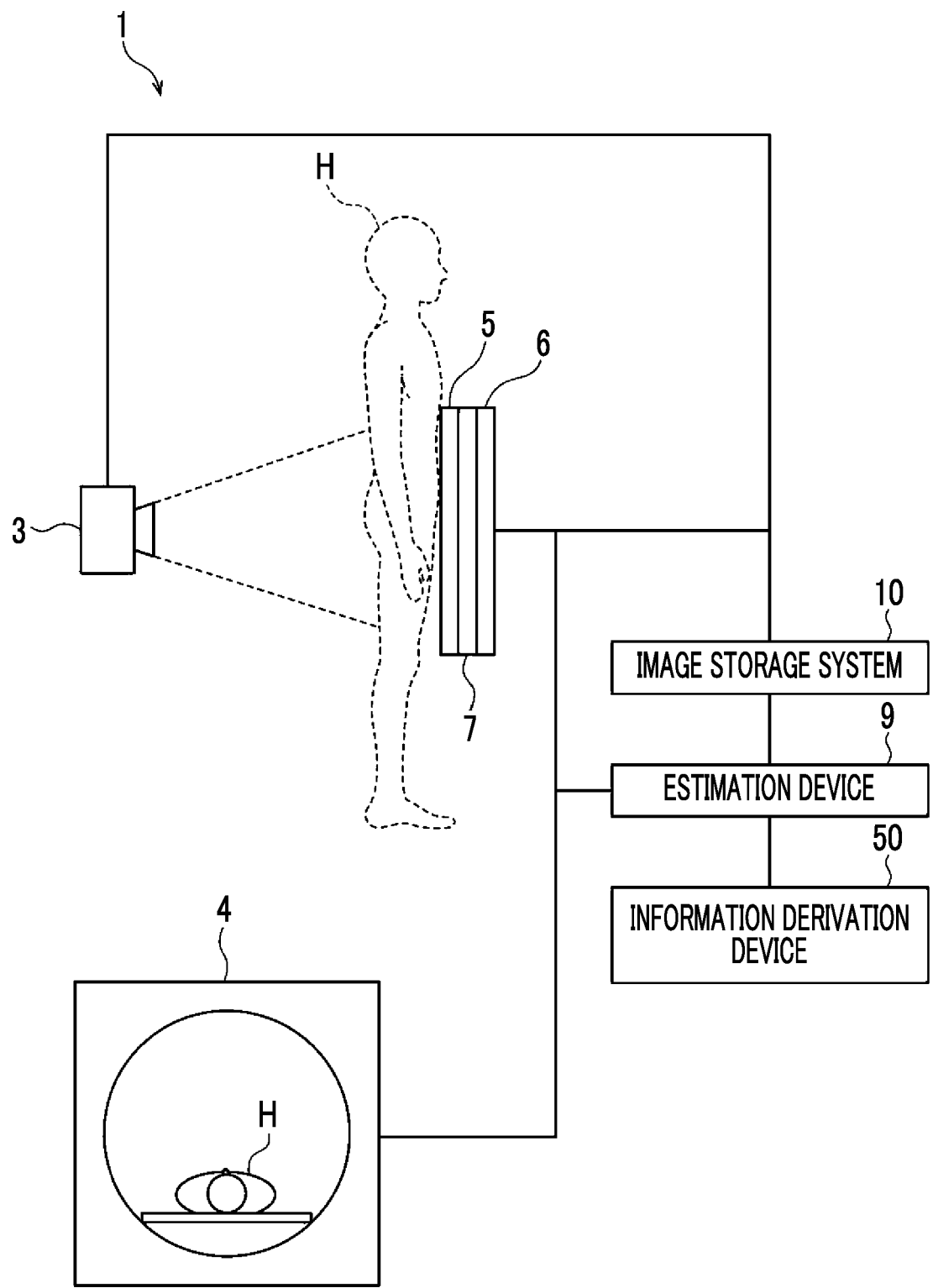
FIG. 1 is a schematic block diagram showing a configuration of a radiography system to which an estimation device according to a first embodiment of the present disclosure is applied.

Hereinafter, embodiments of the present disclosure will be described with reference to the drawings. FIG. 1 is a schematic block diagram showing a configuration of a radiography system to which an estimation device according to a first embodiment of the present disclosure is applied. As shown in FIG. 1, the radiography system according to the first embodiment comprises an imaging apparatus 1, a computed tomography (CT) device 4, an image storage system 9, an estimation device 10 according to the first embodiment, and an information derivation device 50. The imaging apparatus 1, the CT device 4, the estimation device 10, and the information derivation device 50 are connected to the image storage system 9 via a network (not shown).

The imaging apparatus 1 is an imaging apparatus that can perform energy subtraction by a so-called one-shot method for converting radiation, such as X-rays, emitted from a radiation source 3 and transmitted through a subject H into energy and irradiating a first radiation detector 5 and a second radiation detector 6 with the converted radiation. At the time of imaging, as shown in FIG. 1, the first radiation detector 5, a radiation energy conversion filter 7 made of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. Therefore, the first radiation image G1 and the second radiation image G2 are acquired by imaging the subject H with the radiation having different energy distributions. The first and second radiation images G1 and G2 are transmitted to the image storage system 9. Both the first radiation image G1 and the second radiation image G2 are front images including a buttock and a lower limb of the subject H.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

In addition, the imaging apparatus 1 can also acquire a simple radiation image G0 which is a simple two-dimensional image of the subject H by performing a simple imaging of the subject H by using only the first radiation detector 5. The imaging for acquiring the first and second radiation images G1 and G2 is referred to as energy subtraction imaging in order to distinguish the imaging from simple imaging. In the present embodiment, the first and second radiation images G1 and G2 acquired by the energy subtraction imaging are used for deriving teacher data for learning of a neural network to be described below. In addition, the simple radiation image G0 acquired by the simple imaging is used for deriving an estimation result relating to a composition of a soft tissue as described below.

The CT device 4 acquires a plurality of tomographic images representing a plurality of tomographic surfaces of the subject H as a three-dimensional CT image V0. The CT value of each pixel (voxel) in the CT image is a numerical value of the radiation absorbance in the composition constituting the human body. The CT value will be described below. In addition, in the present embodiment, the CT device 4 is used for deriving the teacher data described below.

The image storage system 9 is a system that stores the image data of the radiation image acquired by the imaging apparatus 1 and the image data of the CT image acquired by the CT device 4. The image storage system 9 extracts an image corresponding to requests from the estimation device 10 and the information derivation device 50 from the stored radiation image and CT image and transmits the extracted image to a request source device. Specific examples of the image storage system 9 include picture archiving and communication systems (PACS). Note that in the present embodiment, the image storage system 9 stores a large amount of teacher data for learning the neural network described below.

Figure 2:
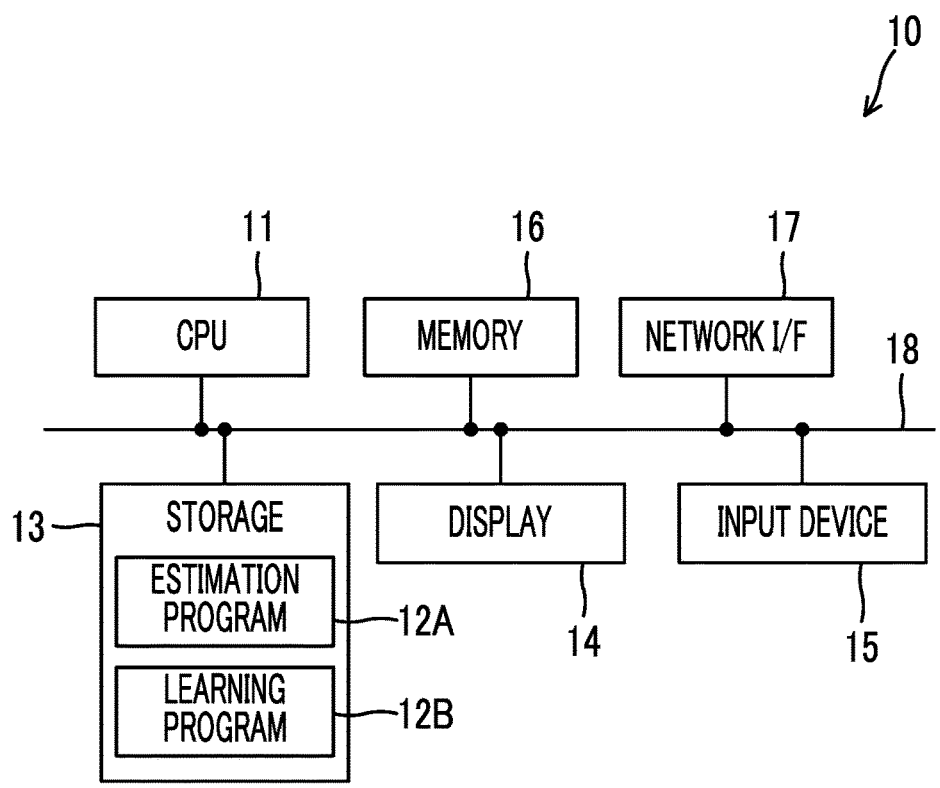
FIG. 2 is a diagram showing a schematic configuration of the estimation device according to the first embodiment.

Then, the estimation device according to the first embodiment will be described. First, a hardware configuration of the estimation device according to the first embodiment will be described with reference to FIG. 2. As shown in FIG. 2, the estimation device 10 is a computer, such as a workstation, a server computer, and a personal computer, and comprises a central processing unit (CPU) 11, a non-volatile storage 13, and a memory 16 as a transitory storage region. In addition, the estimation device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores an estimation program 12A and a learning program 12B installed in the estimation device 10. The CPU 11 reads out the estimation program 12A and the learning program 12B from the storage 13, expands the estimation program 12A and the learning program 12B in the memory 16, and executes the expanded estimation program 12A and the expanded learning program 12B.

Note that the estimation program 12A and the learning program 12B are stored in a storage device of the server computer connected to the network or in a network storage in a state of being accessible from the outside, and are downloaded and installed in the computer that configures the estimation device 10 in response to the request. Alternatively, the estimation program 12A and the learning program 12B are distributed in a state of being recorded on a recording medium, such as a digital versatile disc (DVD) or a compact disc read only memory (CD-ROM), and are installed in the computer that configures the estimation device 10 from the recording medium.

Figure 3:
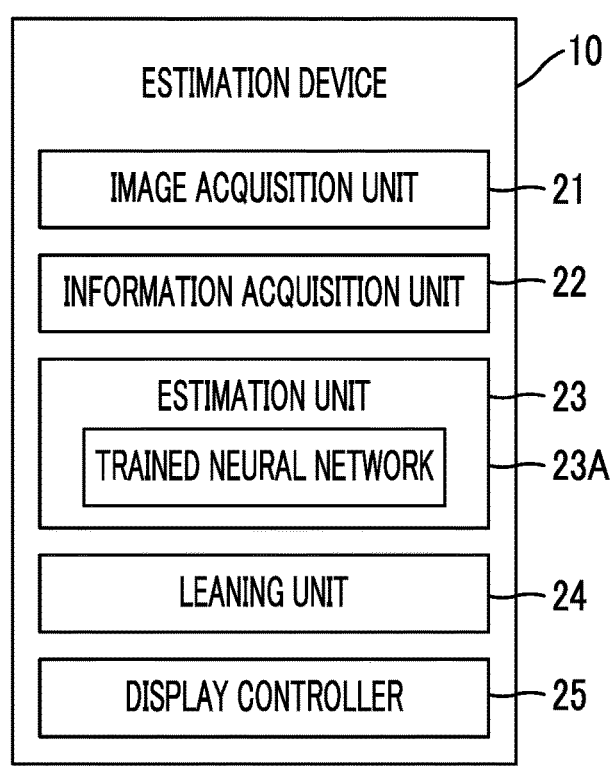
FIG. 3 is a diagram showing a functional configuration of an estimation device according to the first embodiment.

Then, a functional configuration of the estimation device according to the first embodiment will be described. FIG. 3 is a diagram showing the functional configuration of the estimation device according to the first embodiment. As shown in FIG. 3, the estimation device 10 comprises an image acquisition unit 21, an information acquisition unit 22, an estimation unit 23, a learning unit 24, and a display controller 25. Further, the CPU 11 functions as the image acquisition unit 21, the information acquisition unit 22, the estimation unit 23, and the display controller 25 by executing the estimation program 12A. In addition, the CPU 11 functions as the learning unit 24 by executing the learning program 12B.

The image acquisition unit 21 acquires, for example, the first radiation image G1 and the second radiation image G2 which are the front images of the periphery of the crotch of the subject H from the first and second radiation detectors 5 and 6 by causing the imaging apparatus 1 to perform the energy subtraction imaging of the subject H. In a case in which the first radiation image G1 and the second radiation image G2 are acquired, an imaging conditions, such as an imaging dose, a radiation quality, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid are set.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging conditions need only be set by input from the input device 15 by an operator. The set imaging condition and the first and second radiation images G1 and G2 acquired by the energy subtraction imaging are transmitted to and stored in the image storage system 9.

In addition, the image acquisition unit 21 acquires the simple radiation image G0 which is the front image of the vicinity of the crotch of the subject H by causing the imaging apparatus 1 to perform the simple imaging of the subject H by using only the first radiation detector 5. The simple radiation image G0 is stored in the storage 13.

Note that in the present embodiment, the first and second radiation images G1 and G2 and the simple radiation image G0 may be acquired by a program separate from the estimation program 12A.

The information acquisition unit 22 acquires the teacher data for learning a neural network, which will be described below, from the image storage system 9 via the network I/F 17.

The estimation unit 23 derives the estimation result relating to the composition of the soft tissue of the subject H from the simple radiation image G0. In the present embodiment, an estimation result of the muscle mass for a predetermined part in the soft region included in the simple radiation image G0 is derived as the estimation result relating to the composition of the soft tissue. Therefore, the estimation unit 23 derives the estimation result relating to the composition of the soft tissue by using a trained neural network 23A that outputs the muscle mass in a case in which the simple radiation image G0 is input.

The learning unit 24 constructs the trained neural network 23A by subjecting the neural network to machine learning using the teacher data. Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 4:
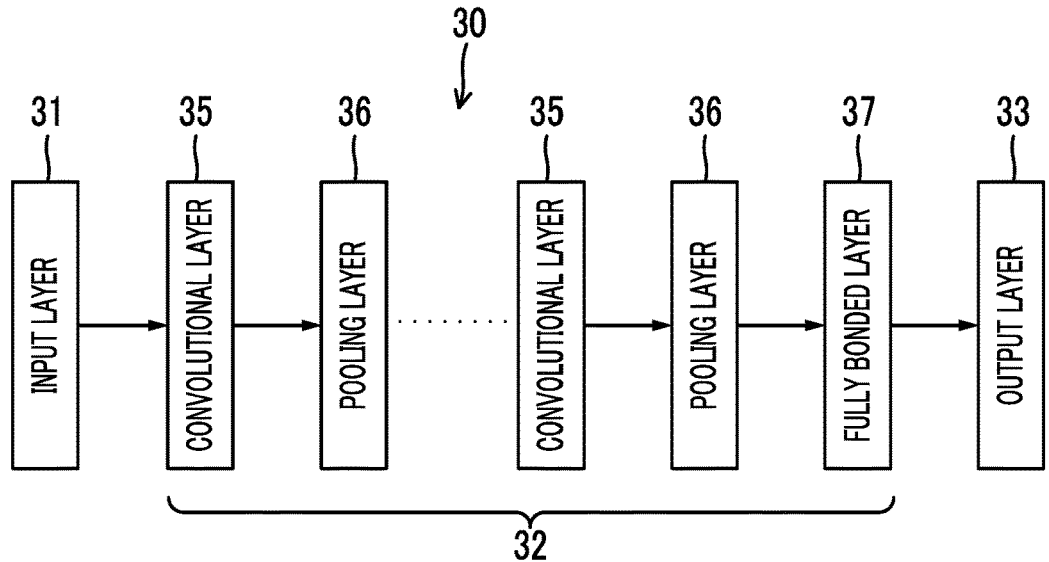
FIG. 4 is a diagram showing a schematic configuration of a neural network used in the present embodiment.

FIG. 4 is a diagram showing the neural network used in the present embodiment. As shown in FIG. 4, a neural network 30 comprises an input layer 31, an interlayer 32, and an output layer 33. The interlayer 32 comprises, for example, a plurality of convolutional layers 35, a plurality of pooling layers 36, and a fully bonded layer 37. In the neural network 30, the fully bonded layer 37 is present in front of the output layer 33. Further, in the neural network 30, the convolutional layer 35 and the pooling layer 36 are alternately disposed between the input layer 31 and the fully bonded layer 37.

Note that a configuration of the neural network 30 is not limited to the example of FIG. 4. For example, the neural network 30 may comprise one convolutional layer 35 and one pooling layer 36 between the input layer 31 and the fully bonded layer 37.

Figure 5:
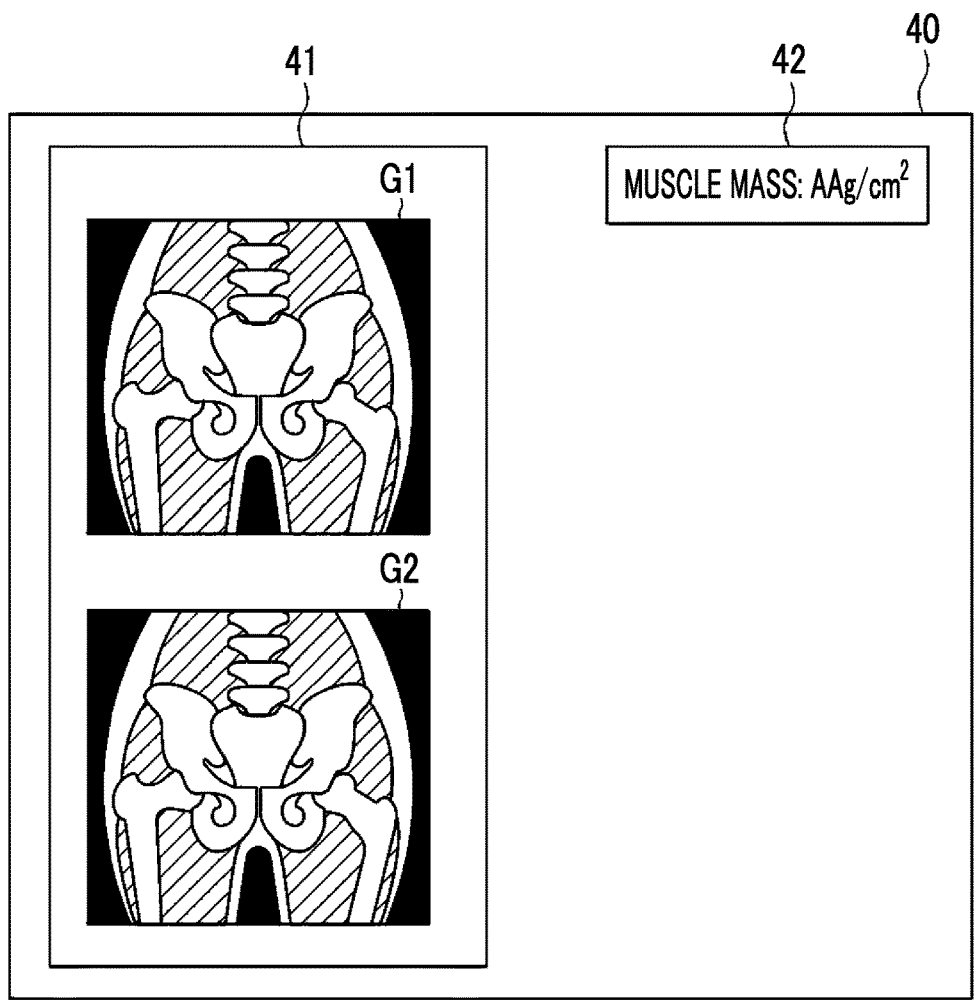
FIG. 5 is a diagram showing teacher data.

FIG. 5 is a diagram showing an example of the teacher data used for learning the neural network. As shown in FIG. 5, teacher data 40 consists of learning data 41 and correct answer data 42. In the present embodiment, the data input to the trained neural network 23A in order to obtain the estimation result relating to the composition of the soft tissue is the simple radiation image G0, but the learning data 41 includes two radiation images of the first radiation image G1 and the second radiation image G2 acquired by the energy subtraction imaging.

The correct answer data 42 is the muscle mass of the predetermined part of the subject from which the learning data 41 is acquired. Note that, in the present embodiment, the predetermined part is the buttock and the upper part of the lower limb. In addition, in the present embodiment, since the muscle mass per unit area is estimated from the two-dimensional simple radiation image G0, the unit of the muscle mass is $(g/cm^2)$. Note that, in the present embodiment, the muscle mass per unit volume may be estimated. In this case, the unit of the muscle mass is $(g/cm^3)$. The muscle mass, which is the correct answer data 42, is derived by the information derivation device 50. The muscle mass, which is the correct answer data 42, is an example of information relating to the composition of the soft tissue of the subject. Hereinafter, the information derivation device 50 will be described.

Figure 6:
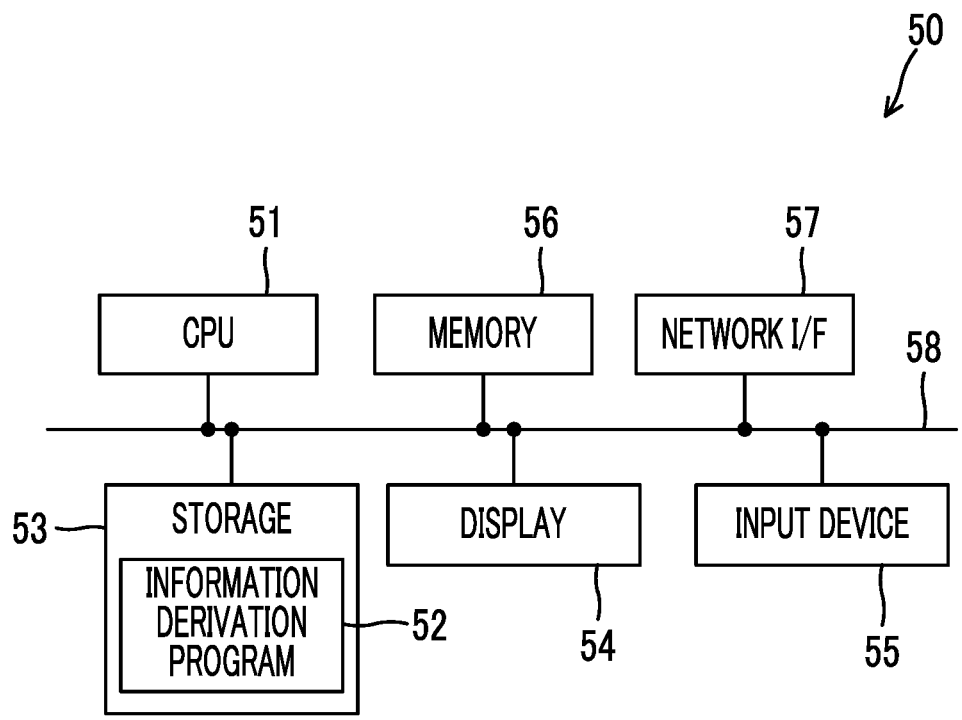
FIG. 6 is a diagram showing a schematic configuration of an information derivation device according to the first embodiment.

FIG. 6 is a schematic block diagram showing a configuration of the information derivation device according to the first embodiment. As shown in FIG. 6, the information derivation device 50 according to the first embodiment is a computer, such as a workstation, a server computer, and a personal computer, and includes a CPU 51, a non-volatile storage 53, and a memory 56 as a transitory storage region. In addition, the information derivation device 50 includes a display 54, such as a liquid crystal display, an input device 55 including a pointing device, such as a keyboard and a mouse, and a network I/F 57 connected to a network (not shown). The CPU 51, the storage 53, the display 54, the input device 55, the memory 56, and the network I/F 57 are connected to a bus 58.

Similar to the storage 13, the storage 53 is realized by the HDD, the SSD, the flash memory, and the like. An information derivation program 52 is stored in the storage 53 as the storage medium. The CPU 51 reads out the information derivation program 52 from the storage 53, expands the read out information derivation program 52 in the memory 56, and executes the expanded information derivation program 52.

Figure 7:
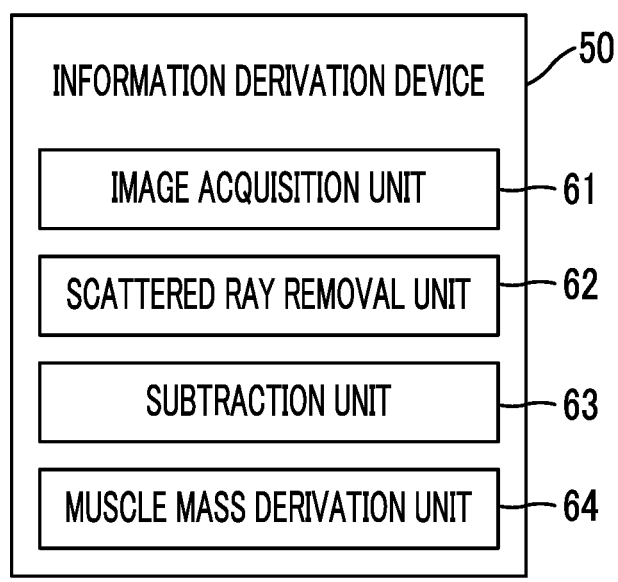
FIG. 7 is a diagram showing a functional configuration of the information derivation device according to the first embodiment.

Then, a functional configuration of the information derivation device according to the first embodiment will be described. FIG. 7 is a diagram showing the functional configuration of the information derivation device according to the first embodiment. As shown in FIG. 7, the information derivation device 50 according to the first embodiment comprises an image acquisition unit 61, a scattered ray removal unit 62, a subtraction unit 63, and a muscle mass derivation unit 64. Further, the CPU 51 executes the information derivation program 52, so that the CPU 51 functions as the image acquisition unit 61, the scattered ray removal unit 62, the subtraction unit 63, and the muscle mass derivation unit 64.

The image acquisition unit 61 acquires the first radiation image G1 and the second radiation image G2, which are the learning data 41, stored in the image storage system 9. Note that the image acquisition unit 61 may acquire the first radiation image G1 and the second radiation image G2 by causing the imaging apparatus 1 to image the subject H in the same manner as the image acquisition unit 21 of the estimation device 10.

In addition, the image acquisition unit 61 also acquires the imaging conditions in a case in which the first radiation image G1 and the second radiation image G2 stored in the image storage system 9 are acquired. The imaging conditions include the imaging dose in a case in which the first radiation image G1 and the second radiation image G2 are acquired, the tube voltage, the SID, the SOD, the presence or absence of the scattered ray removal grid, and the like.

Here, each of the first radiation image G1 and the second radiation image G2 includes a scattered ray component based on the radiation scattered in the subject H in addition to a primary ray component of the radiation transmitted through the subject H. Therefore, the scattered ray removal unit 62 removes the scattered ray component from the first radiation image G1 and the second radiation image G2. For example, the scattered ray removal unit 62 may remove the scattered ray component from the first radiation image G1 and the second radiation image G2 by applying a method disclosed in JP2015-043959A. In a case in which a method disclosed in JP2015-043959A or the like is used, the derivation of the body thickness distribution of the subject H and the derivation of the scattered ray component for removing the scattered ray component are performed at the same time.

Hereinafter, the removal of the scattered ray component from the first radiation image G1 will be described, but the removal of the scattered ray component from the second radiation image G2 can also be performed in the same manner. First, the scattered ray removal unit 62 acquires a virtual model of the subject H having an initial body thickness distribution $T0(x,y)$. The virtual model is data virtually representing the subject H of which a body thickness in accordance with the initial body thickness distribution $T0(x,y)$ is associated with a coordinate position of each pixel of the first radiation image G1. Note that the virtual model of the subject H having the initial body thickness distribution $T0(x,y)$ may be stored in the storage 53 of the information derivation device 50 in advance. In addition, the scattered ray removal unit 62 may calculate a body thickness distribution $T(x,y)$ of the subject H based on the SID and the SOD included in the imaging conditions. In this case, the initial body thickness distribution $T0(x,y)$ can be obtained by subtracting the SOD from the SID.

Next, the scattered ray removal unit 62 generates, based on the virtual model, an image obtained by combining an estimated primary ray image in which a primary ray image obtained by imaging the virtual model is estimated and an estimated scattered ray image in which a scattered ray image obtained by imaging the virtual model is estimated as an estimated image in which the first radiation image G1 obtained by imaging the subject H is estimated.

Next, the scattered ray removal unit 62 corrects the initial body thickness distribution $T0(x,y)$ of the virtual model such that a difference between the estimated image and the first radiation image G1 is small. The scattered ray removal unit 62 repeatedly performs the generation of the estimated image and the correction of the body thickness distribution until the difference between the estimated image and the first radiation image G1 satisfies a predetermined termination condition. The scattered ray removal unit 62 derives the body thickness distribution in a case in which the termination condition is satisfied as the body thickness distribution $T(x,y)$ of the subject H. In addition, the scattered ray removal unit 62 removes the scattered ray component included in the first radiation image G1 by subtracting the scattered ray component in a case in which the termination condition is satisfied from the first radiation image G1.

Figure 8:
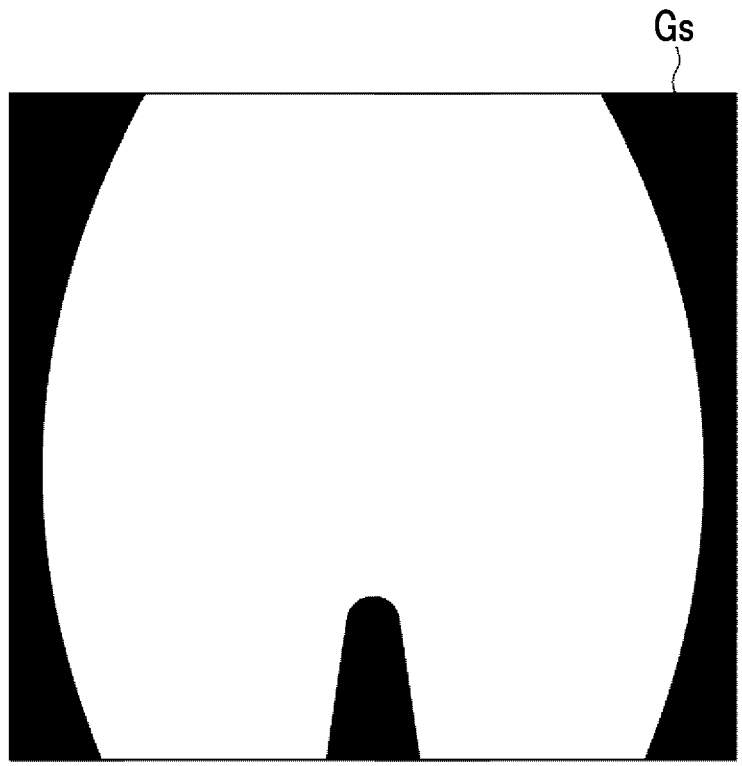
FIG. 8 is a diagram showing a soft part image.

The subtraction unit 63 derives a soft part image Gs obtained by extracting the soft part of the subject H from the first and second radiation images G1 and G2 by performing the energy subtraction processing. Note that, in the first and second radiation images G1 and G2 in the subsequent processing, the scattered ray component is removed. In a case in which the soft part image Gs is derived, the subtraction unit 63 performs weighting subtraction between the corresponding pixels with respect to the first and second radiation images G1 and G2 as shown in Expression (1) to generate the soft part image Gs in which the soft part of the subject H included in each of the radiation images G1 and G2 is extracted, as shown in FIG. 8. In Expression (1), $\alpha$ is a weighting coefficient.

$$Gs(x,y)=G1(x,y)-\alpha \times G2(x,y) \tag{1}$$

The muscle mass derivation unit 64 derives the muscle mass for each pixel in the soft region in the soft part image Gs based on the pixel value. The soft tissue includes the muscle tissue, the fat tissue, the blood, and the water. In the muscle mass derivation unit 64 according to the first embodiment, a tissue other than the fat tissue in the soft tissue is regarded as the muscle tissue. That is, in the muscle mass derivation unit 64 according to the first embodiment, a non-fat tissue including the blood and the water in the muscle tissue is handled as the muscle tissue.

Figure 9:
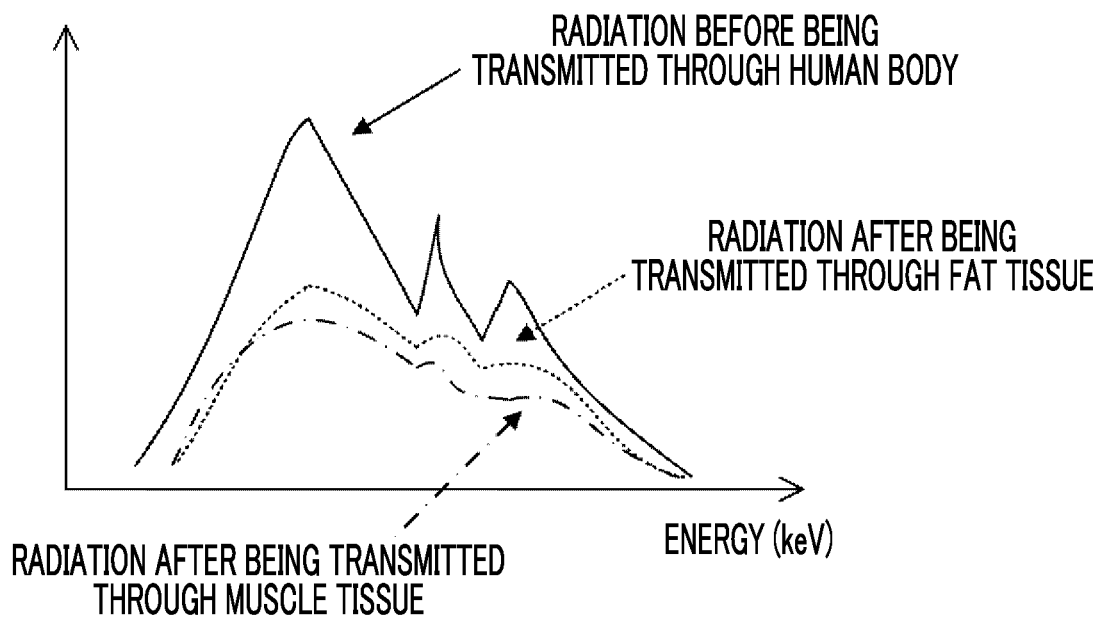
FIG. 9 is a diagram showing an example of energy spectra of radiation after being transmitted through a muscle tissue and radiation after being transmitted through a fat tissue.

The muscle mass derivation unit 64 separates the muscle and the fat from the soft part image Gs by using a difference in an energy characteristic between the muscle tissue and the fat tissue. As shown in FIG. 9, the dose of the radiation after being transmitted through the subject H is lower than the dose of the radiation before being incident on the subject H, which is a human body. In addition, since the energy absorbed by the muscle tissue and the energy absorbed by the fat tissue is different and attenuation coefficients are different, the energy spectra of the radiation after being transmitted through the muscle tissue and the radiation after being transmitted through the fat tissue in the radiation after being transmitted through the subject H are different. As shown in FIG. 9, the energy spectrum of the radiation transmitted through the subject H and emitted to each of the first radiation detector 5 and the second radiation detector 6 depends on a body composition of the subject H, specifically, a ratio between the muscle tissue and the fat tissue. Since the fat tissue is more likely to transmit the radiation than the muscle tissue, the dose of the radiation after being transmitted through the human body is smaller in a case in which the ratio of the muscle tissue is larger than the ratio of the fat tissue.

Therefore, the muscle mass derivation unit 64 separates the muscle and the fat from the soft part image Gs by using the difference in the energy characteristic between the muscle tissue and the fat tissue described above. That is, the muscle mass derivation unit 64 generates a muscle image from the soft part image Gs. In addition, the muscle mass derivation unit 64 derives the muscle mass of each pixel based on the pixel value of the muscle image.

Note that a specific method by which the muscle mass derivation unit 64 separates the muscle and the fat from the soft part image Gs is not limited, but as an example, the muscle mass derivation unit 64 according to the first embodiment generates the muscle image from the soft part image Gs by Expression (2) and Expression (3). Specifically, first, the muscle mass derivation unit 64 derives a muscle ratio rm(x,y) at each pixel position (x,y) in the soft part image Gs by Expression (2). Note that, in Expression (2), $\mu m$ is a weighting coefficient depending on an attenuation coefficient of the muscle tissue, and $\mu f$ is a weighting coefficient depending on an attenuation coefficient of the fat tissue. In addition, $\Delta(x,y)$ represents a concentration difference distribution. The concentration difference distribution is a distribution of a concentration change on the image, which is seen from a concentration obtained by making the radiation reach the first radiation detector 5 and the second radiation detector 6 without transmitted through the subject H. The distribution of the concentration change on the image is calculated by subtracting the concentration of each pixel in the region of the subject H from the concentration in a blank region obtained by directly emitting the radiation in the soft part image Gs to the first radiation detector 5 and the second radiation detector 6.

$$rm(x,y)=\{\mu f-\Delta(x,y)/T(x,y)\}/(\mu f-\mu m) \tag{2}$$

Moreover, the muscle mass derivation unit 64 generates a muscle image Gm from the soft part image Gs by Expression (3). Note that x and y in Expression (3) are the coordinates of each pixel of the muscle image Gm.

$$Gm(x,y)=rm(x,y) \times Gs(x,y) \tag{3}$$

The muscle mass derivation unit 64 need only derive the pixel value of the muscle image Gm as the muscle mass for each pixel. On the other hand, the muscle ratio rm for each pixel may be derived as the muscle mass. In addition, as shown in Expression (4), the muscle mass derivation unit 64 may derive muscle mass M(x,y) (g/cm$^2$) for each pixel of the muscle image Gm by multiplying each pixel (x,y) of the muscle image Gm by the coefficient K1(x,y) representing a relationship between a predetermined pixel value and the muscle mass.

$$M(x,y)=K1(x,y) \times Gm(x,y) \tag{4}$$

In addition, in the first embodiment, the muscle mass derivation unit 64 derives the muscle mass of the predetermined part. In the present embodiment, the muscle mass of the predetermined part refers to a representative value of the muscle mass for each pixel of a region in the soft part image Gs corresponding to the predetermined part. In the present embodiment, since the predetermined part is the buttock and the upper part of the lower limb, a representative value of the muscle mass for each pixel of the region corresponding to the buttock and the upper part of the lower limb in the soft part image Gs is treated as the muscle mass of the buttock and the upper part of the lower limb. An average value, a median value, a minimum value, a maximum value, and the like can be used as the representative value. In the present embodiment, the representative value of the muscle mass of the predetermined part is used as the correct answer data 42.

The muscle mass, which is used as the correct answer data 42, is derived at the same time as the time when the learning data 41 is acquired, and is transmitted to the image storage system 9. In the image storage system 9, the learning data 41 and the correct answer data 42 are stored in association with each other as the teacher data 40. Note that, in order to improve the robustness of the learning, the teacher data 40 including, as learning data 41, an image obtained by performing at least one of enlargement/reduction, contrast change, movement, in-plane rotation, inversion, or noise addition on the same image may be additionally created and stored.

Figure 10:
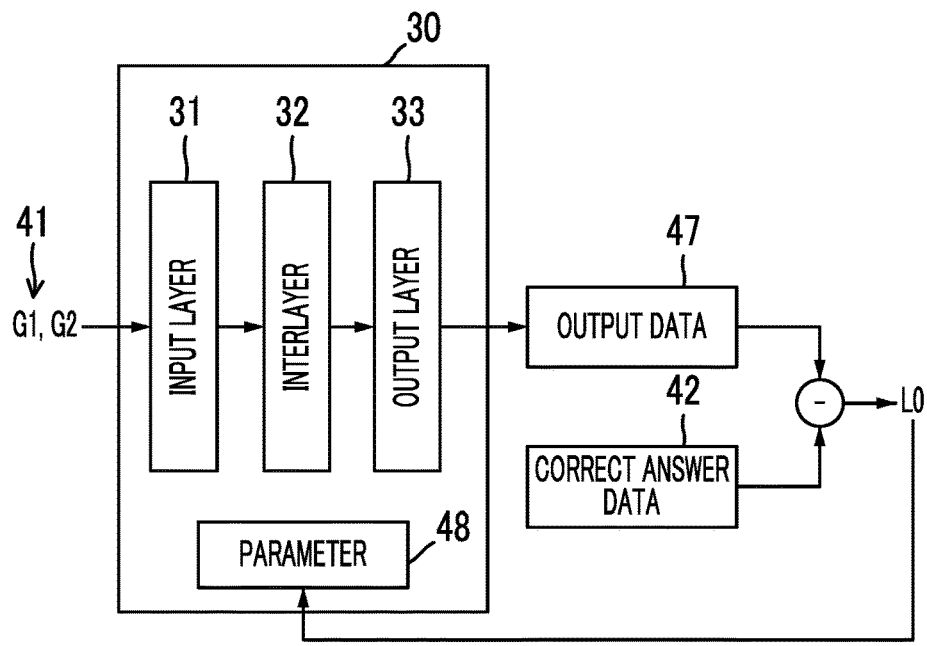
FIG. 10 is a diagram for describing learning of the neural network.

The description will be returned to the estimation device 10. The learning unit 24 trains the neural network using a large amount of the teacher data 40. FIG. 10 is a diagram for describing learning of the neural network 30. In a case in which the neural network 30 learns, the learning unit 24 inputs the learning data 41, that is, the first and second radiation images G1 and G2 to the input layer 31 of the neural network 30. Further, the learning unit 24 outputs the muscle mass of the predetermined part as output data 47 from the output layer 33 of the neural network 30. Further, the learning unit 24 derives a difference between the output data 47 and the correct answer data 42 as a loss L0.

The learning unit 24 trains the neural network 30 based on the loss L0. Specifically, the learning unit 24 adjusts a kernel coefficient in the convolutional layer 35, a weight of the bond between the layers, a weight of the bond in the fully bonded layer 37, and the like (hereinafter referred to as a parameter 48) such that the loss L0 is reduced. For example, an error backpropagation method can be used as a method for adjusting the parameter 48. The learning unit 24 repeats the adjustment of the parameter 48 until the loss L0 is equal to or smaller than a predetermined threshold value. As a result, in a case in which the simple radiation image G0 is input, the parameter 48 is adjusted so as to output the muscle mass of the predetermined part, and the trained neural network 23A is constructed. The constructed trained neural network 23A is stored in the storage 13.

Figure 11:
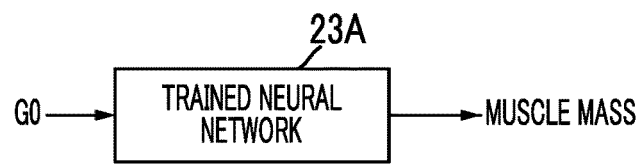
FIG. 11 is a conceptual diagram of processing performed by a trained neural network.

FIG. 11 is a conceptual diagram of processing performed by the trained neural network 23A. As shown in FIG. 11, in a case in which the simple radiation image G0 of a patient is input to the trained neural network 23A constructed as described above, the trained neural network 23A outputs the muscle mass of the predetermined part included in the input simple radiation image G0.

Figure 12:
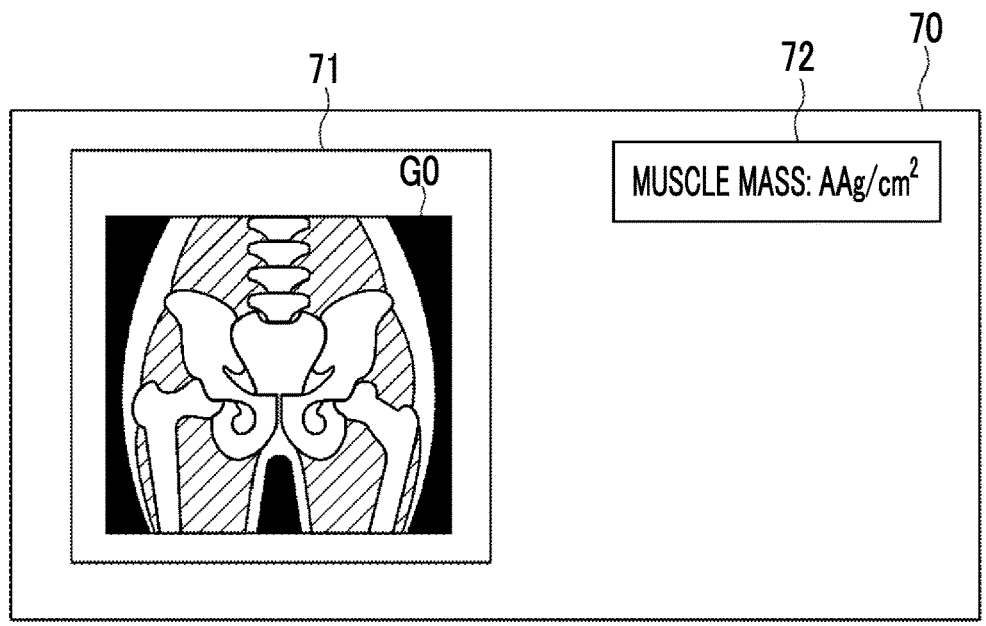
FIG. 12 is a diagram showing a display screen of an estimation result.

The display controller 25 displays the estimation result of the muscle mass estimated by the estimation unit 23 on the display 14. FIG. 12 is a diagram showing a display screen of the estimation result. As shown in FIG. 12, a display screen 70 has an image display region 71 and a muscle mass display region 72. The simple radiation image G0 of the subject H is displayed in the image display region 71. In addition, in the muscle mass display region 72, the representative value of the muscle mass of the predetermined part derived from the muscle mass for each pixel of the simple radiation image G0 estimated by the estimation unit 23 is displayed.

Figure 13:
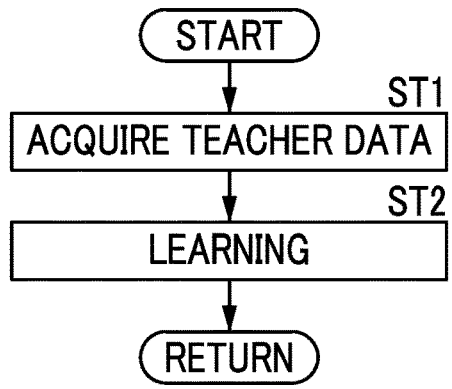
FIG. 13 is a flowchart of learning processing performed in the first embodiment.

Then, the processing performed in the first embodiment will be described. FIG. 13 is a flowchart showing learning processing performed in the first embodiment. First, the information acquisition unit 22 acquires the teacher data 40 from the image storage system 9 (step ST1), and the learning unit 24 inputs the learning data 41 included in the teacher data 40 to the neural network 30 to output the muscle mass and trains the neural network 30 using the loss L0 based on the difference from the correct answer data 42 (step ST2), and the processing returns to step ST1. Further, the learning unit 24 repeats the processing of steps ST1 and ST2 until the loss L0 reaches the predetermined threshold value, and terminates the learning processing. Note that the learning unit 24 may terminate the learning processing by repeating the learning a predetermined number of times. As a result, the learning unit 24 constructs the trained neural network 23A.

Figure 14:
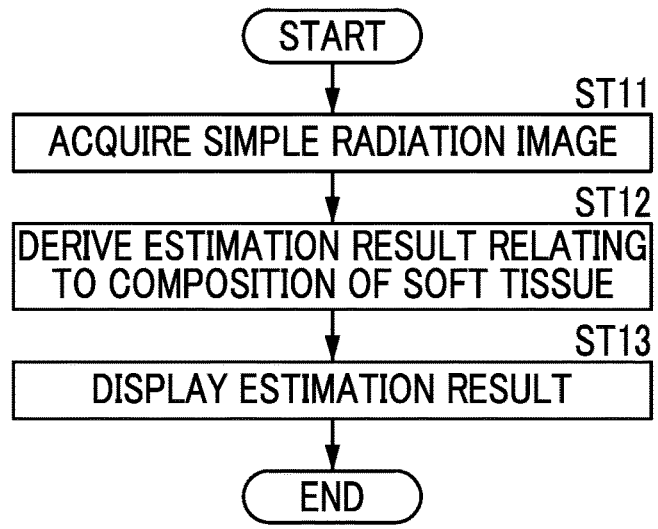
FIG. 14 is a flowchart showing estimation processing performed in the first embodiment.

Then, estimation processing in the first embodiment will be described. FIG. 14 is a flowchart showing estimation processing performed in the first embodiment. Note that the simple radiation image G0 is acquired by the imaging and stored in the storage 13. In a casein which an instruction for starting the processing is input from the input device 15, the image acquisition unit 21 acquires the simple radiation image G0 from the storage 13 (step ST11). Then, the estimation unit 23 derives the estimation result relating to the composition of the soft tissue from the simple radiation image G0 (step ST12). Further, the display controller 25 displays the estimation result relating to the composition of the soft tissue derived by the estimation unit 23 on the display 14 together with the simple radiation image G0 (step ST13), and terminates the processing.

As described above, in the present embodiment, the estimation result relating to the composition of the soft tissue of the subject H included in the simple radiation image G0 is derived by using the trained neural network 23A constructed by performing learning with the first and second radiation images G1 and G2 as teacher data. Here, in the present embodiment, the two radiation images, the first and second radiation images G1 and G2, are used for learning the neural network. Therefore, the trained neural network 23A can derive the estimation result relating to the composition of the soft tissue from the simple radiation image G0 with higher accuracy as compared with a case in which one radiation image and the information relating to the composition of the soft tissue are used as the teacher data. Therefore, according to the present embodiment, the estimation result relating to the composition of the soft tissue can be derived with higher accuracy.

Note that, in the first embodiment, the muscle mass is derived as the correct answer data 42, but the present disclosure is not limited to this. Disease information representing an affection risk of a predetermined disease or a disease level of the predetermined disease may be derived as the correct answer data 42. Hereinafter, this case will be described as a second embodiment.

Figure 15:
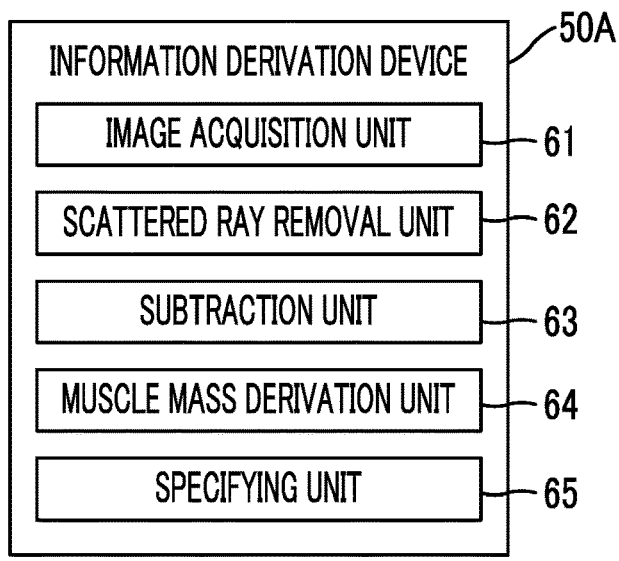
FIG. 15 is a diagram showing a functional configuration of an information derivation device according to a second embodiment.

FIG. 15 is a diagram showing a functional configuration of an information derivation device according to the second embodiment. Note that, in FIG. 15, the same reference numerals are assigned to the same configurations as those in FIG. 7, and the detailed description thereof will be omitted. As shown in FIG. 15, an information derivation device 50A according to the second embodiment further comprises a specifying unit 65 with respect to the information derivation device 50 according to the first embodiment.

The specifying unit 65 specifies the disease information representing the affection risk of the predetermined disease or the disease level of the predetermined disease based on the muscle mass of the predetermined part derived by the muscle mass derivation unit 64 and the correspondence relationship information.

The correspondence relationship information is information representing a correspondence relationship between disease information representing the affection risk of the predetermined disease or the disease level of the predetermined disease, and the muscle mass of the predetermined part.

In general, there is a disease in which a relationship between the muscle mass and the affection risk is known. For example, it is known that the muscle takes some of glucose in blood and of a blood glucose level is adjusted. Therefore, in a case in which the muscle mass is decreased, the blood glucose level is increased, and the affection risk of diabetes is increased. In particular, the decrease of the muscle mass of the lower limb tends to correspond to the affection risk of the diabetes. Therefore, regarding the diabetes, information representing a correspondence relationship between the muscle mass of the thigh, which is a part of the upper part of the lower limb as the predetermined part, and the affection risk of the diabetes is used as the correspondence relationship information. Specific examples thereof include the correspondence relationship information in which, for each age, an average value of the muscle masses of the thigh is defined as a reference value, and a higher affection risk is associated as the muscle mass is smaller than the reference value and has a greater deviation amount from the reference value.

In addition, for example, in a case of sarcopenia, it is known that, in a case in which disease progresses, that is, in a case in which the disease level becomes high, the muscle mass, in particular, the muscle mass of the limbs tends to be decreased. Therefore, regarding the sarcopenia, information representing the correspondence relationship between the muscle mass of the limbs as the predetermined part and the disease level (progression degree) of the sarcopenia is set as the correspondence relationship information. Specific examples thereof include the correspondence relationship information in which, for each age, an average value of the muscle masses of the limbs is defined as a reference value, and a higher disease level is associated as the muscle mass is smaller than the reference value and has a greater deviation amount from the reference value.

Note that the information derivation device 50A may store the correspondence relationship information corresponding to a plurality of types of diseases in the storage 53 as described above, or may store the correspondence relationship information for a specific disease in the storage 53.

As described above, the specifying unit 65 according to the second embodiment specifies the disease information representing the affection risk of the predetermined disease or the disease level of the predetermined disease by using the correspondence relationship information according to the part (imaging part) of the subject that appears in the first radiation image G1 and the second radiation image G2.

Figure 16:
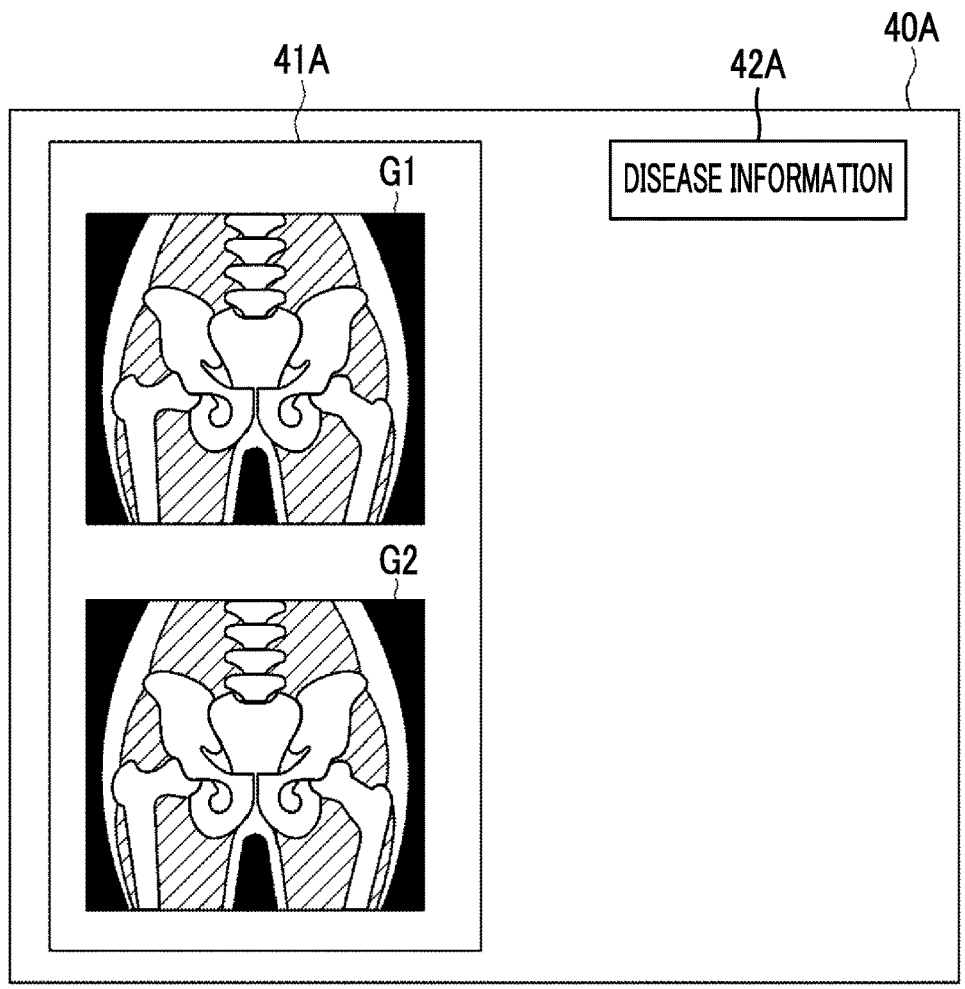
FIG. 16 is a diagram showing teacher data derived in the second embodiment.

In the second embodiment, the disease information derived by the information derivation device 50A is used as the correct answer data of the teacher data. FIG. 16 is a diagram showing the teacher data derived in the second embodiment. As shown in FIG. 16, teacher data 40A consists of learning data 41A including the first and second radiation images G1 and G2, and correct answer data 42A which is the disease information.

By subjecting the neural network to learning using the teacher data 40A shown in FIG. 16, it is possible to construct the trained neural network 23A that outputs the disease information as the estimation result relating to the composition of the soft tissue in a case in which the simple radiation image G0 is input.

Note that, in the first embodiment, the muscle mass is derived as the correct answer data 42, but the present disclosure is not limited to this. The falling-down rate may be derived as the correct answer data 42. Hereinafter, this case will be described as a third embodiment.

Figure 17:
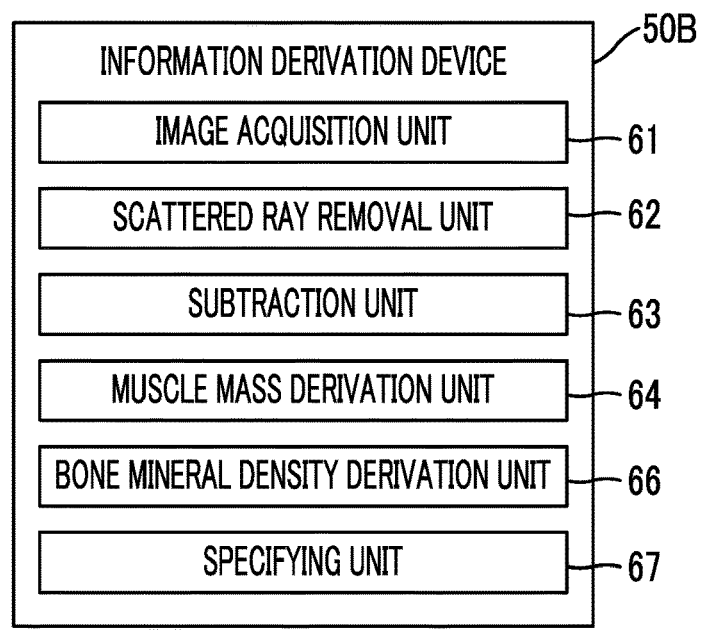
FIG. 17 is a diagram showing a functional configuration of an information derivation device according to a third embodiment.

FIG. 17 is a diagram showing a functional configuration of an information derivation device according to the third embodiment. Note that, in FIG. 17, the same reference numerals are assigned to the same configurations as those in FIG. 7, and the detailed description thereof will be omitted. As shown in FIG. 17, an information derivation device 50B according to the third embodiment further comprises a bone mineral density derivation unit 66 and a specifying unit 67 with respect to the information derivation device 50 according to the first embodiment.

Figure 18:
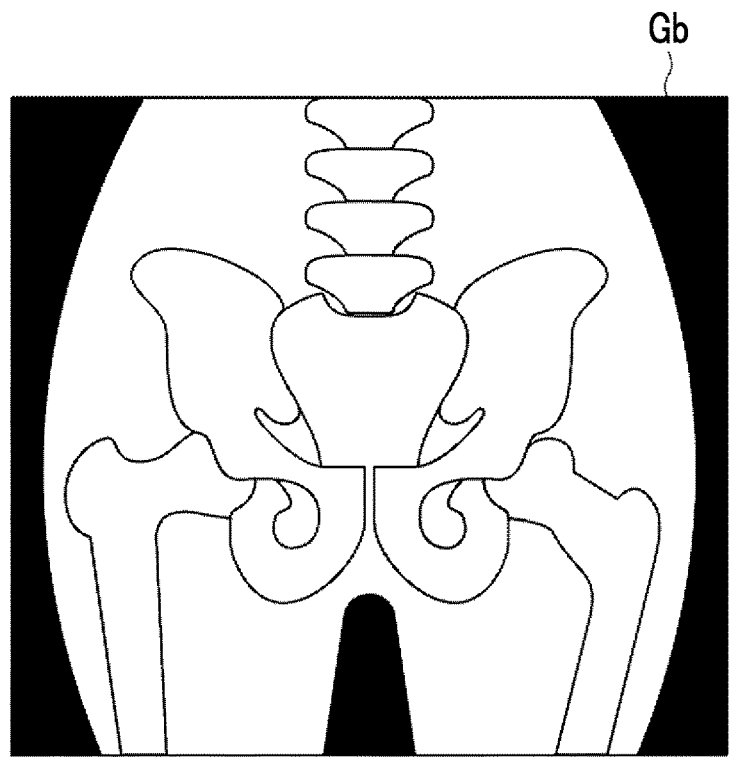
FIG. 18 is a diagram showing a bone part image.

Note that, in the third embodiment, the subtraction unit 63 derives a bone part image Gb obtained by extracting the bone part of the subject H from the first and second radiation images G1 and G2 by performing the energy subtraction processing. Note that, in the first and second radiation images G1 and G2 in the subsequent processing, the scattered ray component is removed. In a case in which the bone part image Gb is derived, the subtraction unit 63 performs weighting subtraction between the corresponding pixels with respect to the first and second radiation images G1 and G2 as shown in Expression (5) to generate the bone part image Gb in which the bone part of the subject H included in each of the radiation images G1 and G2 is extracted, as shown in FIG. 18. In Expression (5), β is a weighting coefficient.

$$Gb(x,y) = \beta \cdot G2(x,y) - G1(x,y) \tag{5}$$

The bone mineral density derivation unit 66 derives the bone mineral density for each pixel of the bone part image Gb. In the third embodiment, the bone mineral density derivation unit 66 derives a bone mineral density B by converting each pixel value of the bone part image Gb into the pixel value of the bone part image acquired under standard imaging conditions. Specifically, the bone mineral density derivation unit 66 derives the bone mineral density by correcting each pixel value of the bone part image Gb by using a correction coefficient acquired from a look-up table described below.

Here, a contrast between the soft part and the bone part in the radiation image is lower as the tube voltage in the radiation source 3 is higher and the energy of the radiation emitted from the radiation source 3 is higher. In addition, in a procedure of the radiation transmitted through the subject H, a low-energy component of the radiation is absorbed by the subject H, and beam hardening occurs in which the radiation energy is increased. The increase in the radiation energy due to the beam hardening is larger as the body thickness of the subject H is larger.

Figure 19:
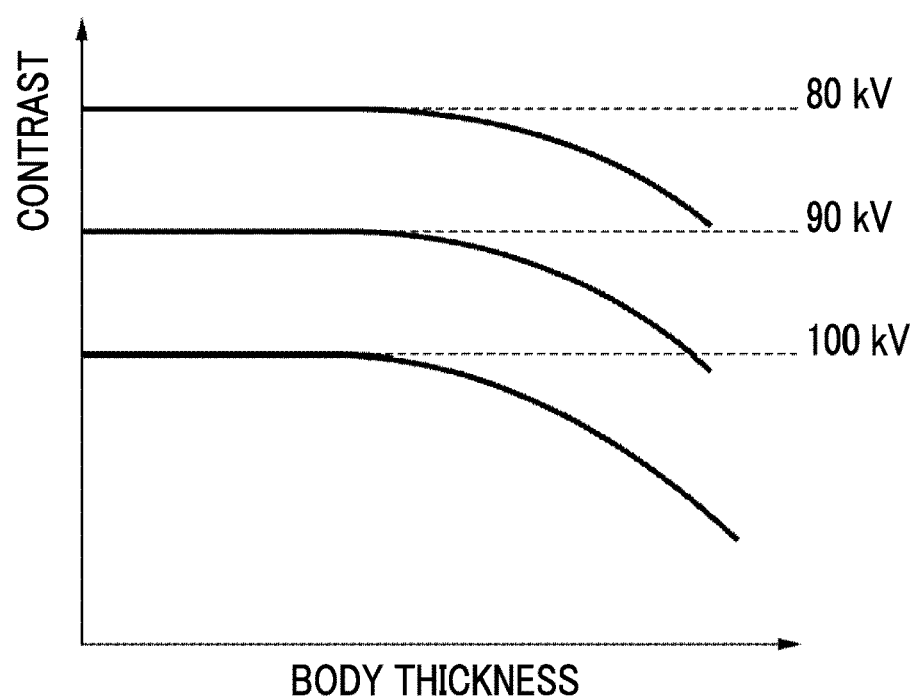
FIG. 19 is a diagram showing a relationship of a contrast between a bone part and a soft part with respect to a body thickness of a subject.

FIG. 19 is a diagram showing a relationship of the contrast between the bone part and the soft part with respect to the body thickness of the subject H. Note that FIG. 19 shows the relationship of the contrast between the bone part and the soft part with respect to the body thickness of the subject H at the three tube voltages of 80 kV, 90 kV, and 100 kV. As shown in FIG. 19, the contrast is lower as the tube voltage is higher. In addition, in a case in which the body thickness of the subject H exceeds a certain value, the contrast is lower as the body thickness is larger. Note that contrast between the bone part and the soft part is higher as the pixel value of the bone region in the bone part image Gb is larger. Therefore, the relationship shown in FIG. 19 shifts to a higher contrast side as the pixel value of the bone region in the bone part image Gb is increased.

In the third embodiment, the look-up table for acquiring the correction coefficient for correcting the difference in the contrast depending on the tube voltage at the time of imaging and the reduction in the contrast due to the influence of the beam hardening in the bone part image Gb is stored in the storage 53 of the information derivation device 50. The correction coefficient is the coefficient for correcting each pixel value of the bone part image Gb.

Figure 20:
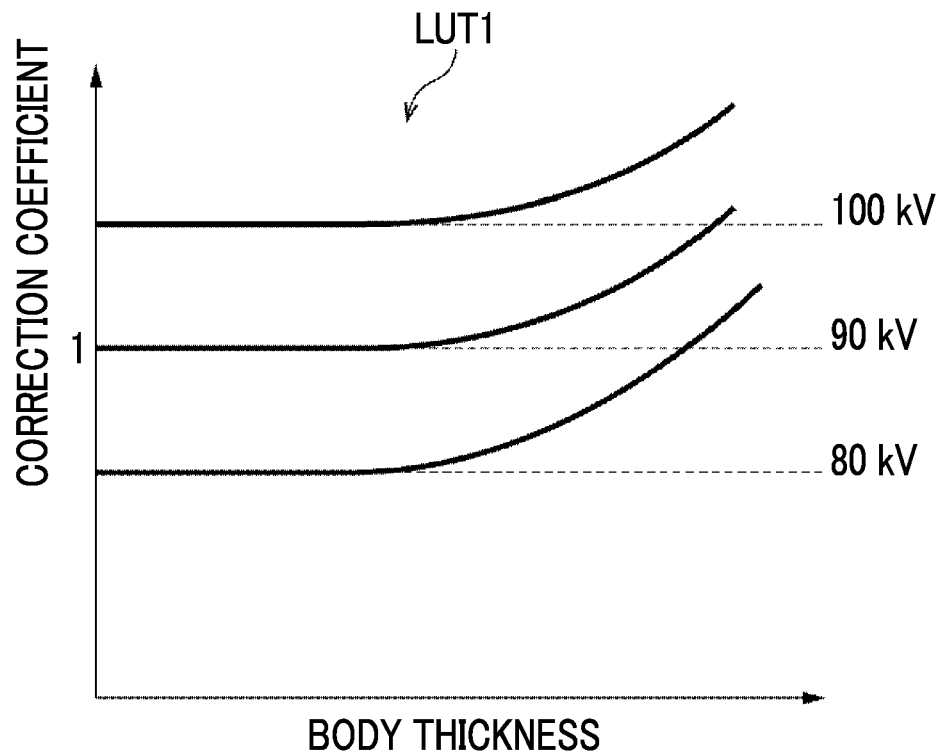
FIG. 20 is a diagram showing an example of a look-up table for acquiring a correction coefficient.

FIG. 20 is a diagram showing an example of the look-up table for acquiring the correction coefficient. In FIG. 20, a look-up table (hereinafter simply referred to as a table) LUT1 in which the standard imaging condition is set to the tube voltage of 90 kV is shown. As shown in FIG. 20, in the table LUT1, the correction coefficient is set to be larger as the tube voltage is higher and the body thickness of the subject H is larger. In the example shown in FIG. 20, since the standard imaging condition is the tube voltage of 90 kV, the correction coefficient is 1 in a case in which the tube voltage is 90 kV and the body thickness is 0. Note that, although the table LUT1 is shown in two dimensions in FIG.

20, the correction coefficient differs depending on the pixel value of the bone region. Therefore, the table LUT1 is actually a three-dimensional table to which an axis representing the pixel value of the bone region is added.

The bone mineral density derivation unit 66 extracts the body thickness distribution T(x,y) of the subject H and a correction coefficient K0(x,y) for each pixel depending on the imaging conditions including a set value of the tube voltage stored in the storage 13 from the table LUT1. Note that, as the body thickness distribution T(x,y), the body thickness distribution in a case in which the termination condition is satisfied need only be used in the scattered ray removal processing performed by the scattered ray removal unit 62. Further, as shown in Expression (6), the bone mineral density derivation unit 66 multiplies each pixel (x,y) of the bone region in the bone part image Gb by the correction coefficient K0(x,y) to derive a bone mineral density B(x,y) (g/cm$^2$) for each pixel of the bone part image Gb. The bone mineral density B(x,y) derived in this way is acquired by imaging the subject H by the tube voltage of 90 kV, which is the standard imaging condition, and represents the pixel value of the bone region included in the radiation image from which the influence of the beam hardening is removed. Therefore, a bone mineral density image in which the derived bone mineral density is used as the pixel value of each pixel is derived by the bone mineral density derivation unit 66.

$$B(x,y)=K0(x,y)\times Gb(x,y) \quad (6)$$

To the specifying unit 67 according to the third embodiment, the information representing the muscle mass is input from the muscle mass derivation unit 64, and the information representing the bone mineral density is input from the bone mineral density derivation unit 66. The specifying unit 67 specifies the falling-down rate (falling-down occurrence rate) of the subject based on the muscle mass of the predetermined part derived by the muscle mass derivation unit 64, the bone mineral density derived by the bone mineral density derivation unit 66, and the correspondence relationship information.

It is known that a probability of a person falling down and the muscle or the muscle strength generally have a correlation relationship. In particular, it is known that there is a correlation relationship with the mass of calf muscle (soleus muscles), which is a part of the lower limb and the mass of the muscle of the buttock that supports the pelvis (gluteus maximus and gluteus medius), or the muscle strength of these muscles.

Figure 21:
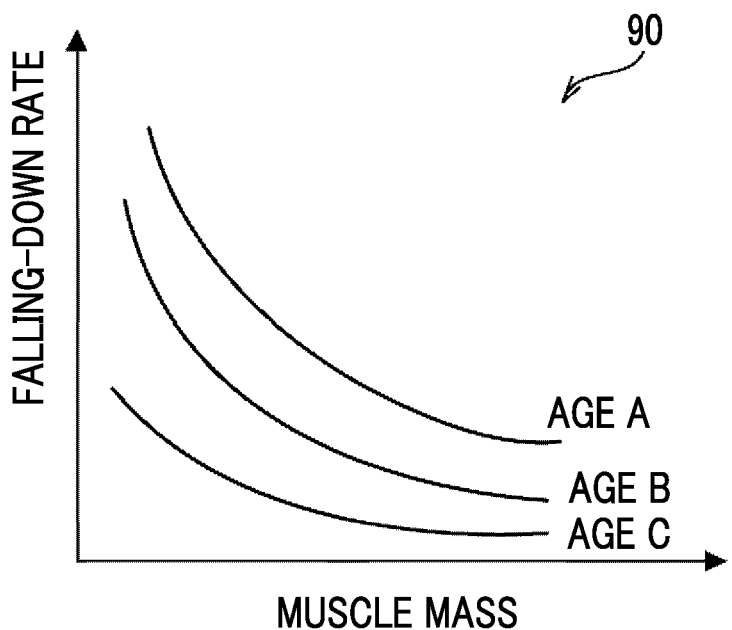
FIG. 21 is a diagram showing correspondence relationship information representing a correlation relationship between a muscle mass and a falling-down rate in the third embodiment.

As an example, FIG. 21 shows the correspondence relationship information 90 representing the relationship correlation between the muscle mass and the falling-down rate for each age. In the correspondence relationship information 90 shown in FIG. 21, the falling-down rate is increased as the muscle mass is decreased at any age. Note that, even in a case in which the muscle mass is the same, as the bone mineral density is decreased, the falling-down rate is increased or a probability of the fracture in a case of falling down. Therefore, the information derivation device 50B according to the third embodiment has the correspondence relationship information 90 for each age as shown in FIG. 21 for each bone mineral density, and a plurality of correspondence relationship information 90 are stored in the storage 53.

Note that, depending on the muscle quality, the muscle strength tends to be greater as the muscle mass is larger. Therefore, instead of the muscle mass, the muscle strength for specifying the falling-down rate may be used as a parameter.

As described above, the specifying unit 67 according to the third embodiment specifies the falling-down rate of the subject by using the correspondence relationship information according to the part (imaging part) of the subject H included in the first radiation image G1 and the second radiation image G2.

Figure 22:
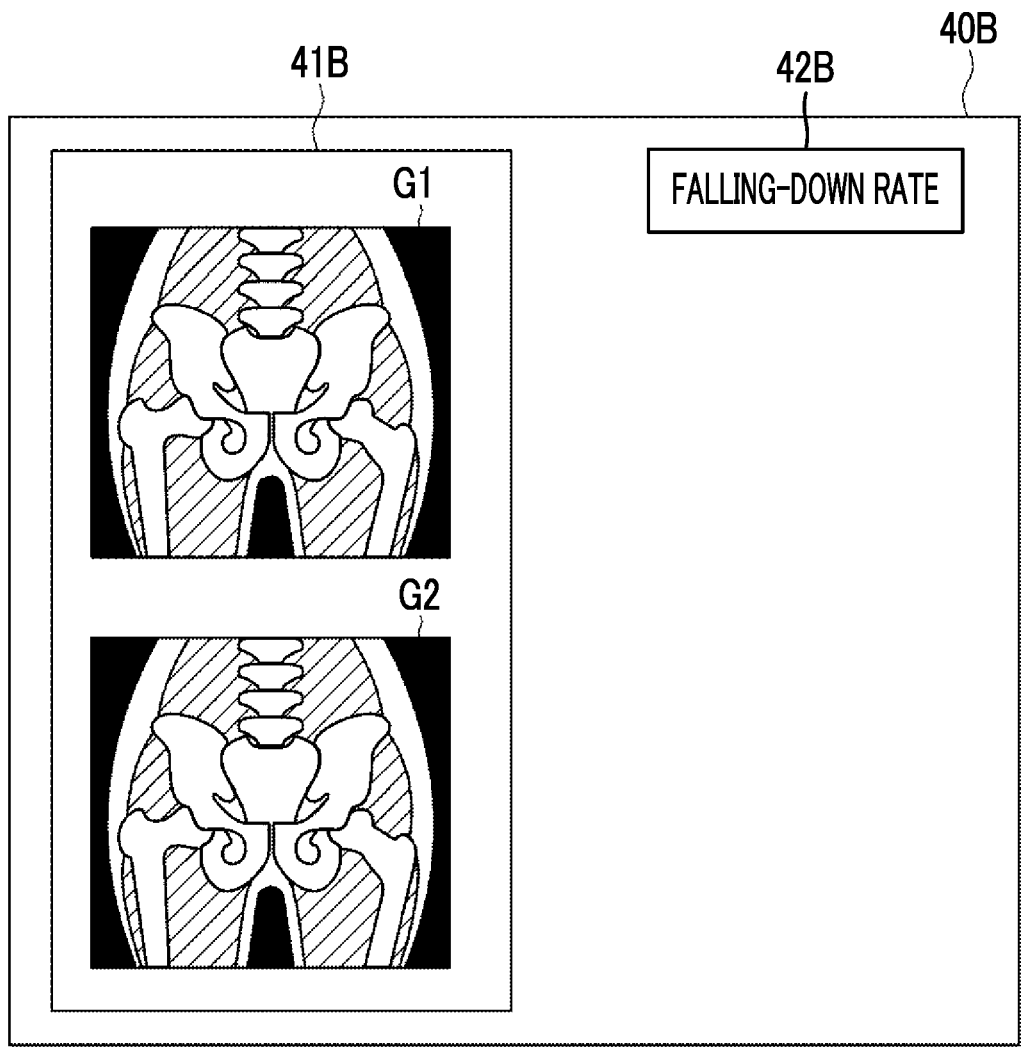
FIG. 22 is a diagram showing teacher data derived in the third embodiment.

In the third embodiment, the falling-down rate derived by the information derivation device 50B is used as the correct answer data of the teacher data. FIG. 22 is a diagram showing the teacher data derived in the third embodiment. As shown in FIG. 22, teacher data 40B consists of learning data 41B including the first and second radiation images G1 and G2, and correct answer data 42B which is the falling-down rate.

By subjecting the neural network to learning using the teacher data 40B shown in FIG. 22, it is possible to construct the trained neural network 23A that outputs the falling-down rate as the estimation result relating to the composition of the soft tissue in a case in which the simple radiation image G0 is input.

Note that the present disclosure is not limited to the first to third embodiments, and for example, the first to third embodiments may be combined. For example, a form may be adopted in which the specifying unit 67 according to the third embodiment specifies the affection risk of the predetermined disease or the disease level of the predetermined disease as the disease information based on the muscle mass of the predetermined part derived by the muscle mass derivation unit 64, the bone mineral density derived by the bone mineral density derivation unit 66, and the correspondence relationship information, and uses the specified disease information as the teacher data. In addition, a form may be adopted in which the specifying unit 65 according to the second embodiment specifies the falling-down rate based on the muscle mass of the predetermined part derived by the muscle mass derivation unit 64 and the correspondence relationship information 90, and uses the specified falling-down rate as the teacher data.

In addition, all of the muscle mass, the disease information, and the falling-down rate, or a plurality items of the muscle mass, the disease information, and the falling-down rate may be specified and used as the teacher data. The trained neural network constructed by learning using such teacher data outputs all of the muscle mass, the disease information, and the falling-down rate, or a plurality items of the muscle mass, the disease information, and the falling-down rate as the estimation result relating to the composition of the soft tissue by inputting the simple radiation image G0.

In addition, the image used for deriving the muscle mass in the first to third embodiments, and the image used for deriving the bone mineral density in the third embodiment may be a minified picture. For example, the muscle mass derivation unit 64 may derive the muscle mass for each pixel of the minified picture obtained by minifying the soft part image Gs. In addition, for example, the bone mineral density derivation unit 66 may derive the bone mineral density for each pixel of the minified picture obtained by minifying the bone part image Gb. In a case in which the minified picture is used as described above, it is possible to reduce noise and to improve a signal-to-noise ratio (SN ratio), so that it is possible to improve the derivation accuracy.

In addition, in the first to third embodiments, the teacher data is derived from the first and second radiation images G1 and G2, but the teacher data may be derived from the CT image acquired by the CT device 4. Hereinafter, this case will be described as a fourth embodiment.

Figure 23:
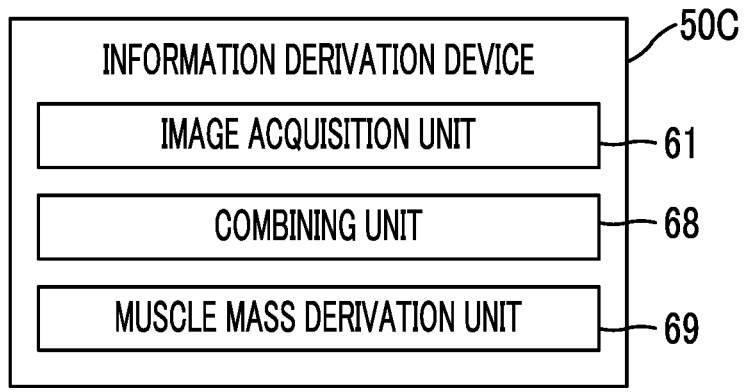
FIG. 23 is a diagram showing a functional configuration of an information derivation device according to a fourth embodiment.

FIG. 23 is a diagram showing a functional configuration of an information derivation device according to the fourth embodiment. Note that, in FIG. 23, the same reference numerals are assigned to the same configurations as those in FIG. 7, and the detailed description thereof will be omitted. As shown in FIG. 23, an information derivation device 50C according to the fourth embodiment comprises a combining unit 68 and a muscle mass derivation unit 69 instead of the scattered ray removal unit 62, the subtraction unit 63, and the muscle mass derivation unit 64 of the information derivation device 50 according to the first embodiment.

In the fourth embodiment, the image acquisition unit 61 acquires, from the image storage system 9, the CT image V0 for deriving the learning data. Note that the image acquisition unit 61 may acquire the CT image V0 by causing the CT device 4 to image the subject H in the same manner as the image acquisition unit 21 of the estimation device 10.

Figure 24:
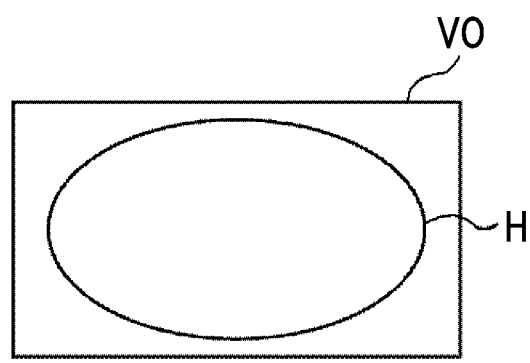
FIG. 24 is a diagram for describing derivation of a composite two-dimensional image.

The combining unit 68 derives the composite two-dimensional image C0 representing the subject H by combining the CT image V0. FIG. 24 is a diagram for describing derivation of the composite two-dimensional image C0. Note that, in FIG. 24, the three-dimensional CT image V0 is shown in two dimensions for the sake of description. As shown in FIG. 24, the subject H is included in a three-dimensional space represented by the CT image V0. The subject H includes a plurality of compositions of the bone part, the fat, the muscle, and the internal organs.

Here, the CT value V0(x,y,z) in each pixel of the CT image V0 can be represented by Expression (7) by using an attenuation coefficient μi of the composition in the pixel and an attenuation coefficient μw of water. (x,y,z) are coordinates representing pixel positions of the CT image V0. Note that, in the following description, the attenuation coefficient means the linear attenuation coefficient unless otherwise specified. The attenuation coefficient represents a degree (ratio) of the radiation attenuation due to absorption or scattering. The attenuation coefficient differs depending on a specific composition (density or the like) and the thickness (mass) of the structure through which radiation is transmitted.

$$V0(x,y,z)=(\mu i-\mu w)/\mu w \times 1000 \quad (7)$$

The attenuation coefficient μw of the water is known. Therefore, by solving Expression (7) for μi, the attenuation coefficient μi of each composition can be calculated as shown in Expression (8).

$$\mu i=V0(x,y,z)\times\mu w/1000+\mu w \quad (8)$$

As shown in FIG. 24, the combining unit 68 virtually irradiates the subject H with the radiation having an irradiation dose I0, and derives the composite two-dimensional image C0 obtained by virtually detecting the radiation transmitted through the subject H by the radiation detector (not shown) installed on a virtual plane 80. Note that the irradiation dose I0 of the virtual radiation and the radiation energy are set depending on predetermined imaging conditions. Specifically, the irradiation dose I0 need only be set by preparing a table corresponding to the imaging conditions, such as the tube voltage, the mAs value, and the SID, and referring to the table. In addition, the radiation energy need only be set by preparing the table depending on the tube voltage and referring to the table. In this case, a reaching dose I1(x,y) for each pixel of the composite two-dimensional image C0 is transmitted through one or more compositions in the subject H. Therefore, the reaching dose I1(x,y) can be derived by Expression (9) by using the attenuation coefficient μi of one or more compositions through which the radiation of the irradiation dose I0 is transmitted. Note that the reaching dose I1(x,y) is the pixel value of each pixel of the composite two-dimensional image C0.

$$I1(x,y)=I0\times\exp(-\int\mu i \cdot dt) \quad (9)$$

Figure 25:
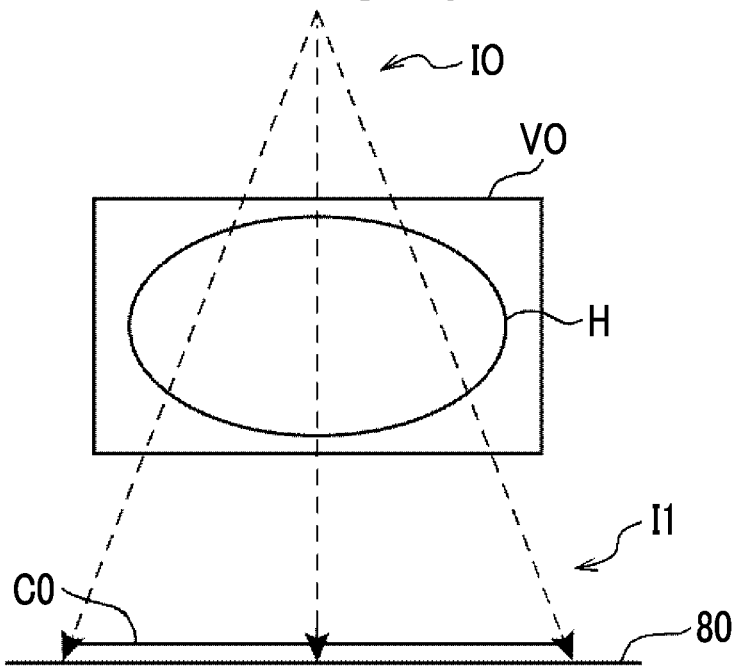
FIG. 25 is a diagram for describing the derivation of the composite two-dimensional image.

Note that in a case in which it is assumed that the radiation source to emit the radiation is a plane light source, as the attenuation coefficient μi used in Expression (9), a value derived from the CT value of the pixels arranged in the vertical direction shown in FIG. 24 by Expression (8) need only be used. In addition, in a case in which it is assumed that the plane light source of the light source to emit the radiation is a point light source, as shown in FIG. 25, based on the geometric positional relationship between the point light source and each position on the virtual plane 80, the pixel on the path of the radiation reaching each pixel need only be specified and the attenuation coefficient μi derived from the CT value of the specified pixel by Expression (8) need only be used.

Figure 26:
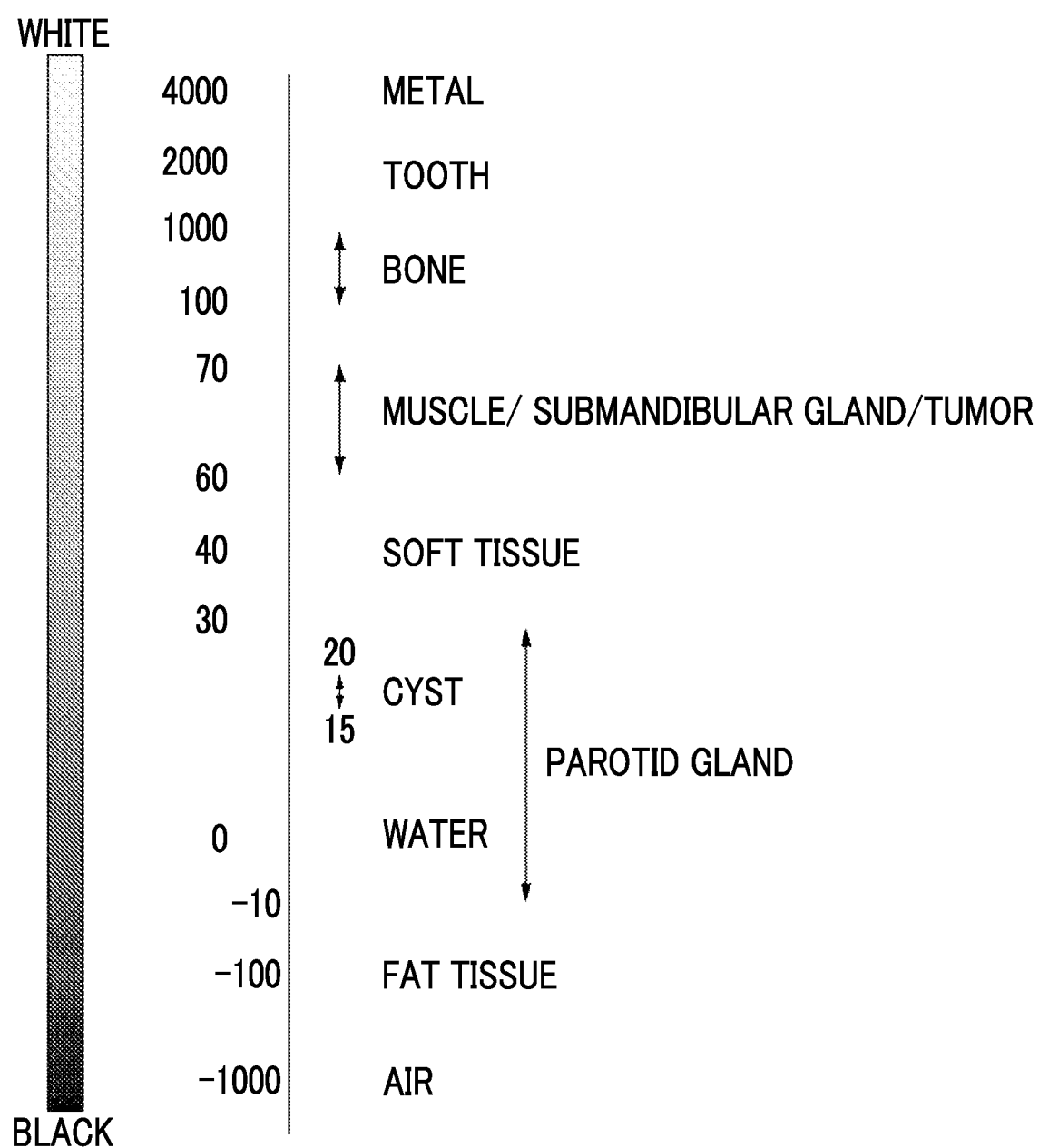
FIG. 26 is a diagram for describing a CT value.

The muscle mass derivation unit 69 derives the muscle mass of the subject H for each pixel of the composite two-dimensional image C0 by using the CT image V0. Here, description for the CT value will be made. FIG. 26 is a diagram for describing the CT value. The CT value is a numerical value of the X-ray absorbance in the human body. Specifically, as shown in FIG. 26, the CT value is determined depending on the composition constituting the human body, such as 0 for the water and −1000 (unit: HU) for the CT value of the air.

The muscle mass derivation unit 69 first specifies the muscle region in the CT image V0 based on the CT value of the CT image V0. Specifically, a region consisting of the pixels having the CT value of 60 to 70 is specified as the muscle region by the threshold value processing. Note that the muscle region may be specified by using the trained neural network that is trained to detect the muscle region from the CT image V0 instead of the threshold value processing. In addition, the muscle region may be specified by displaying the CT image V0 on the display 54 and receiving designation of the muscle region by the manual operation in the displayed CT image V0.

Here, the density ρ [g/cm$^3$] per unit volume of the composition in each pixel of the CT image can be derived by Expression (10) from the attenuation coefficient μi [1/cm] of the composition and the mass attenuation coefficient μe [cm$^2$/g] of the composition.

$$\rho=\mu i/\mu e \quad (10)$$

Figure 27:
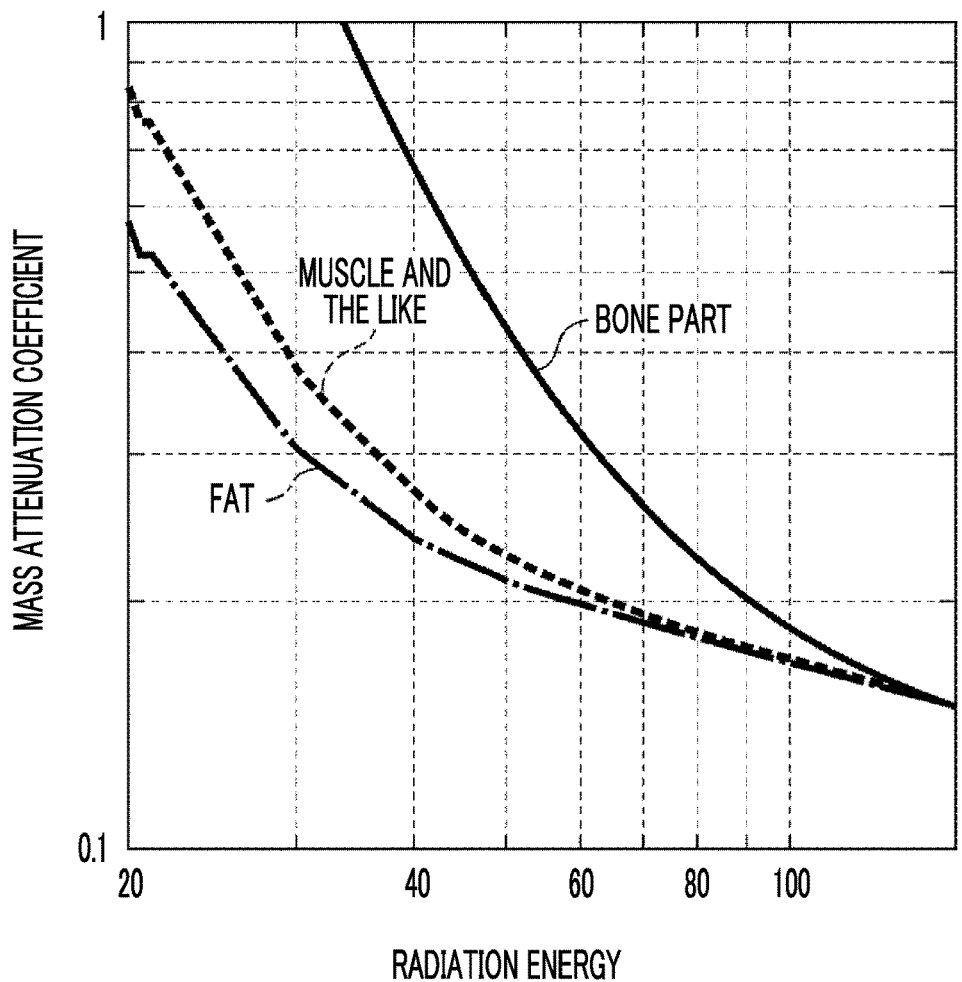
FIG. 27 is a diagram showing a relationship between radiation energy and a mass attenuation coefficient.

FIG. 27 is a diagram showing a relationship between the radiation energy and the mass attenuation coefficient in various compositions of the human body. FIG. 27 shows the relationship between the radiation energy and the mass attenuation coefficient for the bone part, the muscle and the like, and the fat. Note that the muscle and the like mean the muscle, the blood, and the water. In the present embodiment, the relationship between the radiation energy and the mass attenuation coefficient, which is shown in FIG. 27, is stored in the storage 53 as a table. In the present embodiment, since the mass attenuation coefficient of the muscle is required, the mass attenuation coefficient of the muscle is acquired by referring to the relationship of the muscle in the table shown in FIG. 27 based on the virtual radiation energy. In addition, the attenuation coefficient μm in each pixel of the muscle region is derived by Expression (8). Further, the muscle density μm per unit volume in each pixel of the muscle region included in the CT image V0 is derived by Expression (10) as the muscle mass.

Note that the CT image V0 is the three-dimensional image, the unit of the muscle mass per unit volume derived by Expression (10) is [g/cm$^3$]. In the present embodiment, the muscle mass derivation unit 69 derives the muscle mass per unit area for each pixel of the composite two-dimensional image C0. Therefore, the muscle mass derivation unit 69 projects the muscle density pm per unit volume derived by Expression (10) onto the virtual plane 80 in the same manner as a case in which the composite two-dimensional image C0 is derived to derive the muscle mass M [g/cm$^2$] per unit area for each pixel of the composite two-dimensional image C0.

Note that, in a case of projection, a representative value of the muscle mass of each pixel of the CT image V0 on the path reaching each pixel of the composite two-dimensional image C0 from the virtual radiation source need only be derived. An integrated value, an average value, a maximum value, a median value, a minimum value, and the like can be used as the representative value. Further, in the present embodiment, the muscle mass derivation unit 69 need only derive the representative value of the muscle mass for the predetermined part. For example, in a case in which the predetermined part is the buttock and the upper part of the lower limb, the muscle mass derivation unit 69 derives the representative value of the muscle mass of each pixel in the region of the buttock and the upper part of the lower limb in the composite two-dimensional image C0. An average value, a median value, a minimum value, a maximum value, and the like can be used as the representative value. In the present embodiment, the representative value of the muscle mass of the buttock and the upper part of the lower limb, which are predetermined parts, are used as the correct answer data.

Figure 28:
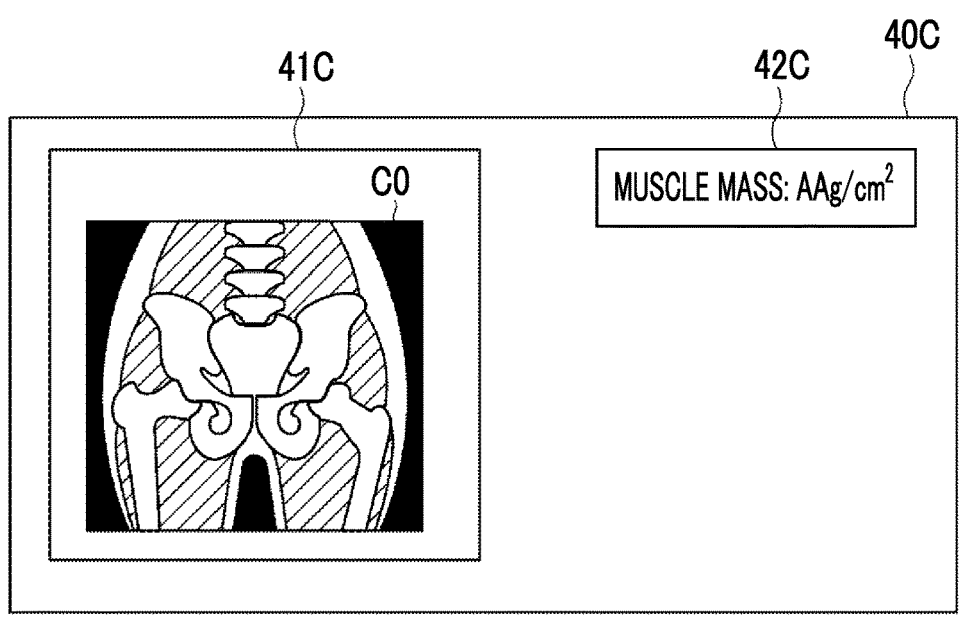
FIG. 28 is a diagram showing teacher data derived in the fourth embodiment.

In the fourth embodiment, the muscle mass derived by the information derivation device 50C is used as the correct answer data of the teacher data. FIG. 28 is a diagram showing the teacher data derived in the fourth embodiment. As shown in FIG. 28, the teacher data 40C consists of the learning data 41C including the composite two-dimensional image C0 and correct answer data 42C which is the muscle mass.

By subjecting the neural network to learning using the teacher data 40C shown in FIG. 28, similar to the first embodiment, it is possible to construct the trained neural network 23A that outputs the muscle mass as the estimation result relating to the composition of the soft tissue in a case in which the simple radiation image G0 is input.

Note that, in the fourth embodiment, the muscle mass is derived from the CT image V0 as the correct answer data, but the present disclosure is not limited to this. Similar to the second embodiment, the disease information representing the affection risk of the predetermined disease or the disease level of the predetermined disease may be derived as the correct answer data. Hereinafter, this case will be described as a fifth embodiment.

Figure 29:
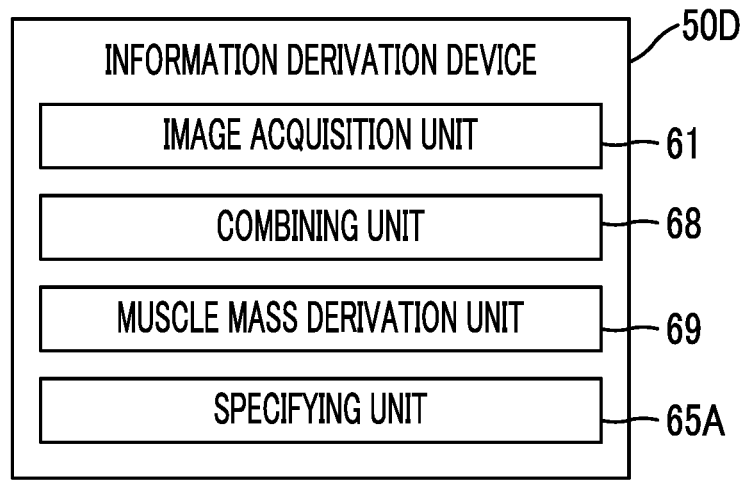
FIG. 29 is a diagram showing a functional configuration of an information derivation device according to a fifth embodiment.

FIG. 29 is a diagram showing a functional configuration of an information derivation device according to the fifth embodiment. Note that, in FIG. 29, the same reference numerals are assigned to the same configurations as those in FIG. 23, and the detailed description thereof will be omitted. As shown in FIG. 29, an information derivation device 50D according to the fifth embodiment further comprises a specifying unit 65A that performs the same processing as the specifying unit 65 of the information derivation device 50A according to the second embodiment with respect to the information derivation device 50C according to the fourth embodiment.

In the fifth embodiment, the specifying unit 65A specifies the disease information representing the affection risk of the predetermined disease or the disease level of the predetermined disease based on the muscle mass of the predetermined part derived from the CT image V0 by the muscle mass derivation unit 69 and the correspondence relationship information.

Figure 30:
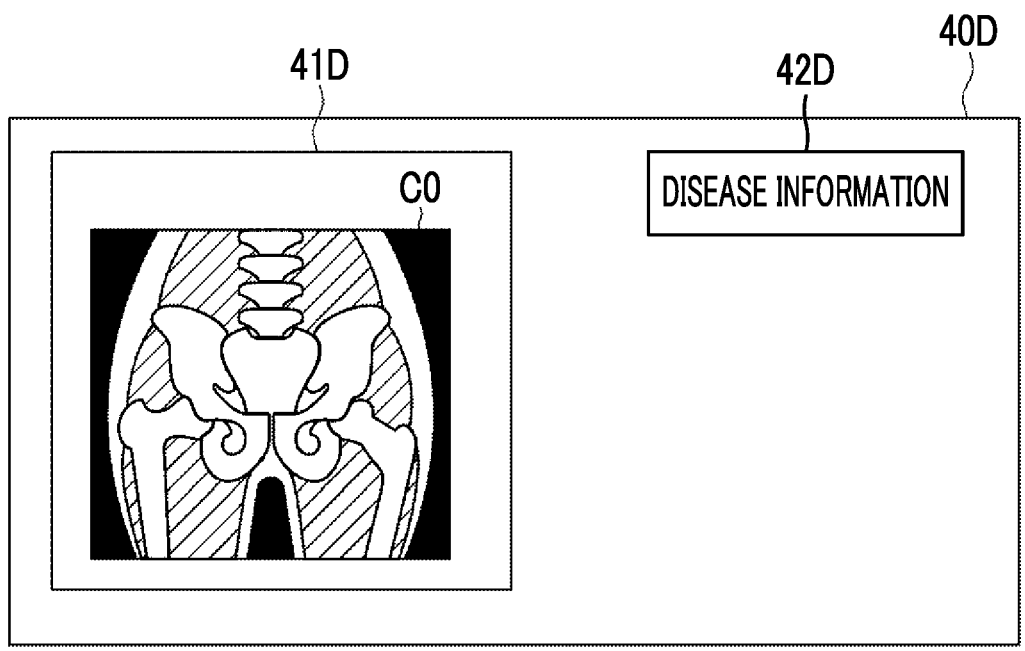
FIG. 30 is a diagram showing teacher data derived in the fifth embodiment.

In the fifth embodiment, the disease information derived by the information derivation device 50D is used as the correct answer data of the teacher data. FIG. 30 is a diagram showing the teacher data derived in the fifth embodiment. As shown in FIG. 30, teacher data 40D consists of learning data 41D including the composite two-dimensional image C0 and correct answer data 42D which is the disease information.

By subjecting the neural network to learning using the teacher data 40D shown in FIG. 30, similar to the second embodiment, it is possible to construct the trained neural network 23A that outputs the disease information as the estimation result relating to the composition of the soft tissue in a case in which the simple radiation image G0 is input.

Note that, in the fourth embodiment, the muscle mass is derived from the CT image V0 as the correct answer data, but the present disclosure is not limited to this. Similar to the third embodiment, the falling-down rate may be derived as the correct answer data. Hereinafter, this case will be described as a sixth embodiment.

Figure 31:
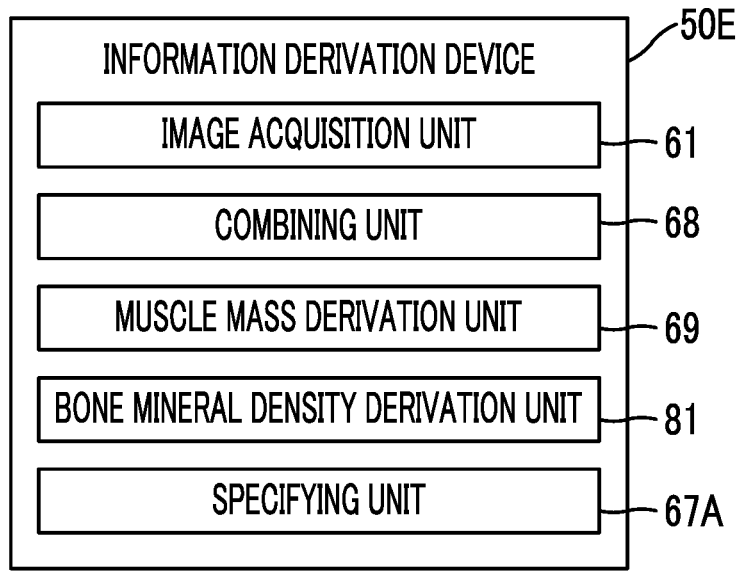
FIG. 31 is a diagram showing a functional configuration of an information derivation device according to a sixth embodiment.

FIG. 31 is a diagram showing a functional configuration of an information derivation device according to the sixth embodiment. Note that, in FIG. 31, the same reference numerals are assigned to the same configurations as those in FIG. 23, and the detailed description thereof will be omitted. As shown in FIG. 31, an information derivation device 50E according to the sixth embodiment further comprises a bone mineral density derivation unit 81 and a specifying unit 67A that performs the same processing as the specifying unit 67 of the information derivation device 50B according to the third embodiment with respect to the information derivation device 50C according to the fourth embodiment.

The bone mineral density derivation unit 81 derives the bone mineral density of the subject H for each pixel of the composite two-dimensional image C0 by using the CT image V0. That is, the bone mineral density derivation unit 81 first specifies the bone region in the CT image V0 based on the CT value of the CT image V0. Specifically, the region consisting of the pixels having the CT value of 100 to 1000 is specified as the bone region by the threshold value processing. Note that the bone region may be specified by using the trained neural network that is trained to detect the bone region from the CT image V0 instead of the threshold value processing. In addition, the bone region may be specified by displaying the CT image V0 on the display 54 and receiving designation of the bone region by a manual operation in the displayed CT image V0.

In the sixth embodiment, since the mass attenuation coefficient of the bone part is required, the mass attenuation coefficient of the bone part is acquired by referring to the relationship of the bone part in the table shown in FIG. 27 based on the virtual radiation energy. In addition, the attenuation coefficient μb in each pixel of the bone region is derived by Expression (8). Further, the bone mineral density ρb per unit volume in each pixel of the bone region included in the CT image V0 is derived by Expression (10).

Note that the CT image V0 is the three-dimensional image, the unit of the bone mineral density per unit volume derived by Expression (10) is [g/cm³]. In the sixth embodiment, the bone mineral density derivation unit 81 derives the bone mineral density per unit area for each pixel of the composite two-dimensional image C0. Therefore, the bone mineral density derivation unit 81 projects the bone mineral density ρb per unit volume derived by Expression (10) onto the virtual plane 80 in the same manner as a case in which the composite two-dimensional image C0 is derived to derive the bone mineral density B [g/cm²] per unit area for each pixel of the composite two-dimensional image C0.

Note that in a case of projection, a representative value of the bone mineral density of each pixel of the CT image V0 on the path reaching each pixel of the composite two-dimensional image C0 from the virtual radiation source need only be derived. An integrated value, an average value, a maximum value, a median value, a minimum value, and the like can be used as the representative value. Further, in the sixth embodiment, the bone mineral density derivation unit 81 need only derive the representative value of the bone mineral density only for the predetermined part. In the present embodiment, since the predetermined part is the buttock and the upper part of the lower limb, the bone mineral density derivation unit 81 derives the representative value of the bone mineral density of each pixel in the region of the buttock and the upper part of the lower limb in the composite two-dimensional image C0. An average value, a median value, a minimum value, a maximum value, and the like can be used as the representative value.

In the sixth embodiment, the specifying unit 67A specifies the falling-down rate based on the muscle mass of the predetermined part derived from the CT image V0 by the muscle mass derivation unit 69, the bone mineral density of the predetermined part derived by the bone mineral density derivation unit 81, and the correspondence relationship information 90 shown in FIG. 21.

Figure 32:
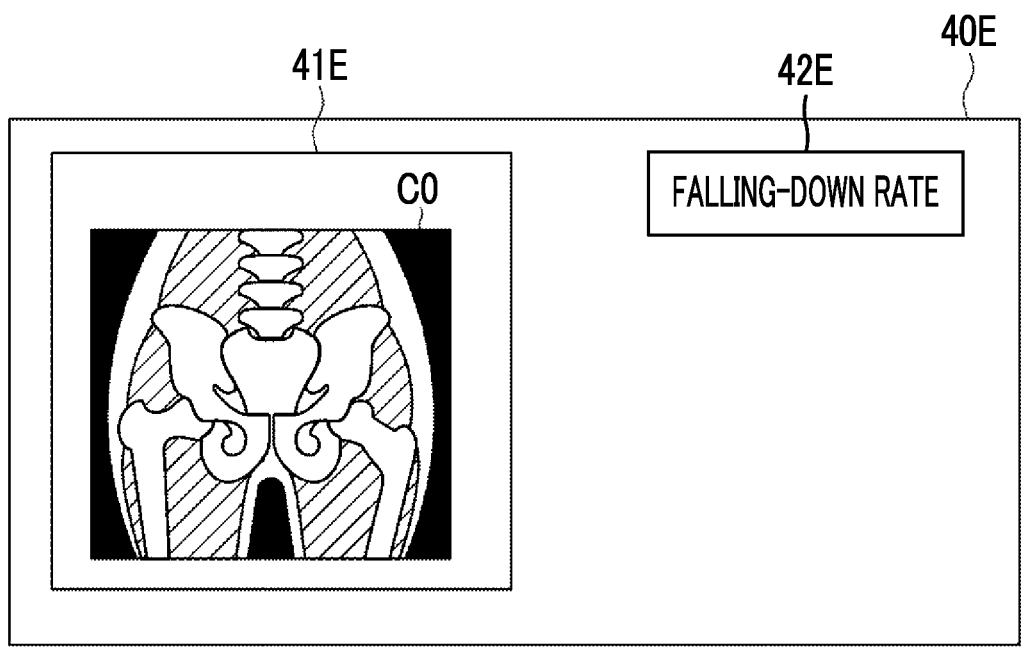
FIG. 32 is a diagram showing teacher data derived in the sixth embodiment.

In the sixth embodiment, the falling-down rate derived by the information derivation device 50E is used as the correct answer data of the teacher data. FIG. 32 is a diagram showing the teacher data derived in the sixth embodiment. As shown in FIG. 32, teacher data 40E consists of learning data 41E including the composite two-dimensional image C0 and correct answer data 42E which is the falling-down rate.

By subjecting the neural network to learning using the teacher data 40E shown in FIG. 32, it is possible to construct the trained neural network 23A that outputs the falling-down rate as the estimation result relating to the composition of the soft tissue in a case in which the simple radiation image G0 is input.

Note that the present disclosure is not limited to the fourth to sixth embodiments, and for example, the fourth to sixth embodiments may be combined. For example, a form may be adopted in which the specifying unit 67A according to the sixth embodiment specifies the disease information representing the affection risk of the predetermined disease or the disease level of the predetermined disease based on the muscle mass of the predetermined part derived by the muscle mass derivation unit 69, the bone mineral density of the predetermined part derived by the bone mineral density derivation unit 81, and the correspondence relationship information, and uses the specified disease information as the teacher data. In addition, a form may be adopted in which the specifying unit 65A according to the fifth embodiment specifies the falling-down rate based on the muscle mass of the predetermined part derived by the muscle mass derivation unit 69 and the correspondence relationship information 90, and uses the specified falling-down rate as the teacher data.

In addition, all of the muscle mass, the disease information, and the falling-down rate, or a plurality items of the muscle mass, the disease information, and the falling-down rate may be specified and used as the teacher data. The trained neural network constructed by learning using such teacher data outputs all of the muscle mass, the disease information, and the falling-down rate, or a plurality items of the muscle mass, the disease information, and the falling-down rate as the estimation result relating to the composition of the soft tissue by inputting the simple radiation image G0.

In addition, in the first embodiment, the muscle mass is derived as the correct answer data, but the present disclosure is not limited to this. The fat mass may be derived as the correct answer data. Hereinafter, this case will be described as a seventh embodiment.

Figure 33:
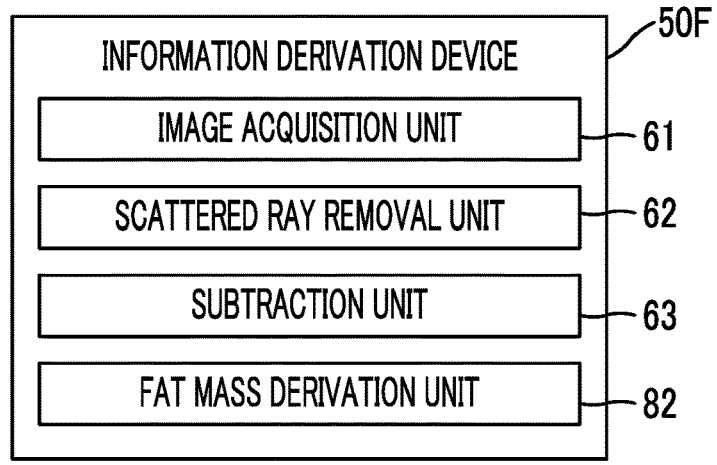
FIG. 33 is a diagram showing a functional configuration of an information derivation device according to a seventh embodiment.

FIG. 33 is a diagram showing a functional configuration of an information derivation device according to the seventh embodiment. Note that, in FIG. 33, the same reference numerals are assigned to the same configurations as those in FIG. 7, and the detailed description thereof will be omitted. As shown in FIG. 33, an information derivation device 50F according to the seventh embodiment comprises a fat mass derivation unit 82 instead of the muscle mass derivation unit 64 provided in the information derivation device 50 according to the first embodiment.

The fat mass derivation unit 82 separates the muscle and the fat from the soft part image Gs by using the difference in the energy characteristic between the muscle tissue and the fat tissue described above. That is, while the muscle mass derivation unit 64 according to the first embodiment derives the muscle image from the soft part image Gs, the fat mass derivation unit 82 generates the fat image from the soft part image Gs. In addition, the fat mass derivation unit 82 derives the fat mass of each pixel based on the pixel value of the fat image.

First, the fat mass derivation unit 82 derives the muscle ratio rm(x,y) at each pixel position (x,y) in the soft part image Gs from Expression (2), similarly to the muscle mass derivation unit 64 according to the first embodiment. Further, a fat ratio rf(x,y) (=1−rm(x,y)) is derived by subtracting the muscle ratio rm(x,y) from 1.

Moreover, the fat mass derivation unit 82 generates a fat image Gf from the soft part image Gs by Expression (11). Note that x and y in Expression (11) are the coordinates of each pixel of the fat image Gf.

$$Gf(x,y) = rf(x,y) \times Gs(x,y) \qquad (11)$$

The fat mass derivation unit 82 need only derive the pixel value of the fat image Gf as the fat mass for each pixel. On the other hand, the fat ratio rf for each pixel may be derived as the fat mass. In addition, as shown in Expression (12), in the fat image Gf, the fat mass F(x,y) (g/cm²) for each pixel of the fat image Gf may be derived by multiplying each pixel (x,y) of the fat image Gf by a coefficient K2 (x,y) representing the relationship between the predetermined pixel value and the fat mass. In this case, the fat mass is the fat mass per unit area, but the fat mass per unit volume may be derived.

$$F(x,y) = K2(x,y) \times Gf(x,y) \qquad (12)$$

Figure 34:
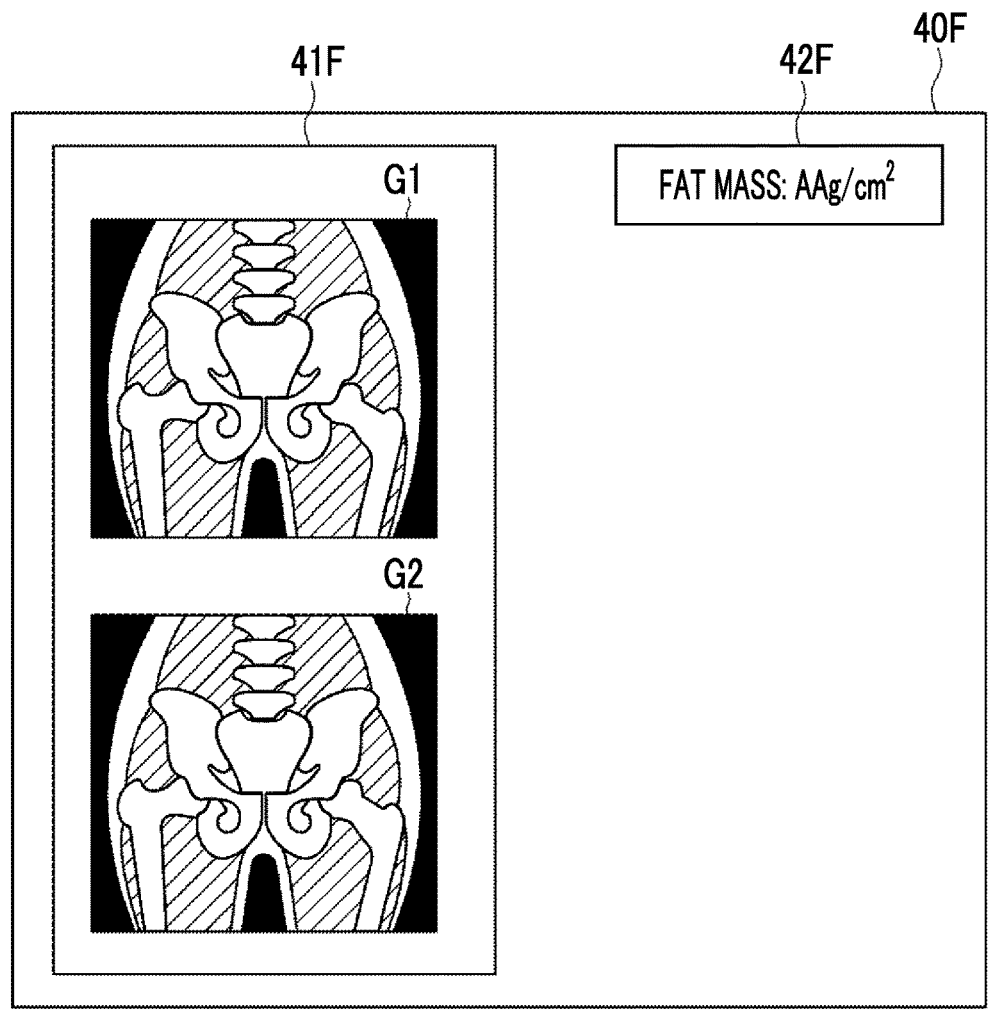
FIG. 34 is a diagram showing teacher data derived in the seventh embodiment.

In the seventh embodiment, the fat mass derived by the information derivation device 50F is used as the correct answer data of the teacher data. FIG. 34 is a diagram showing the teacher data derived in the seventh embodiment. As shown in FIG. 34, teacher data 40F consists of learning data 41F including the first and second radiation images G1 and G2, and correct answer data 42F which is the fat mass.

By subjecting the neural network to learning using the teacher data 40F shown in FIG. 34, it is possible to construct the trained neural network 23A that outputs the fat mass as the estimation result relating to the composition of the soft tissue in a case in which the simple radiation image G0 is input.

In addition, in the fourth embodiment, the muscle mass is derived as the correct answer data, but the present disclosure is not limited to this. The fat mass may be derived as the correct answer data. Hereinafter, this case will be described as an eighth embodiment.

Figure 35:
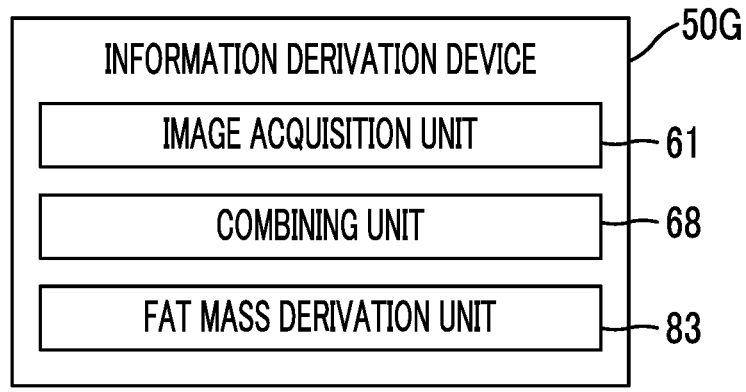
FIG. 35 is a diagram showing a functional configuration of an information derivation device according to an eighth embodiment.

FIG. 35 is a diagram showing a functional configuration of an information derivation device according to the eighth embodiment. Note that, in FIG. 35, the same reference numerals are assigned to the same configurations as those in FIG. 7, and the detailed description thereof will be omitted. As shown in FIG. 35, an information derivation device 50G according to the eighth embodiment comprises a fat mass derivation unit 83 instead of the muscle mass derivation unit 69 provided in the information derivation device 50C according to the fourth embodiment.

The fat mass derivation unit 83 derives the fat mass of the subject H for each pixel of the composite two-dimensional image C0 by using the CT image V0. That is, the fat mass derivation unit 83 first specifies the fat region in the CT image V0 based on the CT value of the CT image V0. Specifically, the region consisting of the pixels having the CT value of about −100, for example, the CT value of −100±10 is specified as the fat region by the threshold value processing. Note that the fat region may be specified by using the trained neural network that is trained to detect the fat region from the CT image V0 instead of the threshold value processing. In addition, the fat region may be specified by displaying the CT image V0 on the display 54 and receiving designation of the fat region by the manual operation in the displayed CT image V0.

Further, the fat mass derivation unit 83 acquires the mass attenuation coefficient of the fat with reference to the relationship with the fat shown in FIG. 27. In addition, the attenuation coefficient pf in each pixel of the fat region is derived by Expression (8). Further, the fat density $\eta f$ per unit volume in each pixel of the fat region included in the CT image V0 is derived by Expression (10) as the fat mass.

Note that the CT image V0 is the three-dimensional image, the unit of the fat mass per unit volume derived by Expression (10) is [g/cm$^3$]. In the present embodiment, the fat mass derivation unit 83 derives the fat mass per unit area for each pixel of the composite two-dimensional image C0. Therefore, the fat mass derivation unit 83 projects the fat density pf per unit volume derived by Expression (10) onto the virtual plane 80 in the same manner as a case in which the composite two-dimensional image C0 is derived to derive the fat mass F [g/cm$^2$] per unit area for each pixel of the composite two-dimensional image C0.

Note that, in a case of projection, a representative value of the fat mass of each pixel of the CT image V0 on the path reaching each pixel of the composite two-dimensional image C0 from the virtual radiation source need only be derived. An integrated value, an average value, a maximum value, a median value, a minimum value, and the like can be used as the representative value. Further, in the present embodiment, the fat mass derivation unit 83 need only derive the representative value of the fat mass for the predetermined part. For example, in a case in which the predetermined part is the abdomen, the fat mass derivation unit 83 derives the representative value of the fat mass of each pixel in an abdominal region in the composite two-dimensional image C0. An average value, a median value, a minimum value, a maximum value, and the like can be used as the representative value.

Figure 36:
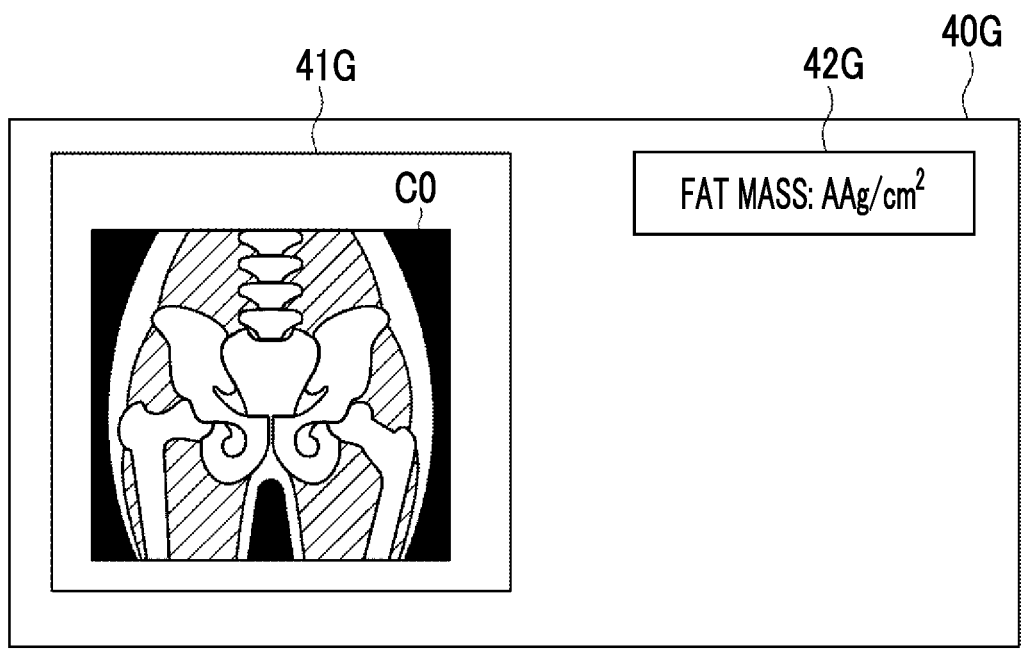
FIG. 36 is a diagram showing teacher data derived in the eighth embodiment.

In the eighth embodiment, the fat mass derived by the information derivation device 50G is used as the correct answer data of the teacher data. FIG. 36 is a diagram showing the teacher data derived in the eighth embodiment. As shown in FIG. 36, teacher data 40G consists of learning data 41G including the composite two-dimensional image C0 and correct answer data 42G which is the fat mass.

By subjecting the neural network to learning using the teacher data 40G shown in FIG. 36, similar to the seventh embodiment, it is possible to construct the trained neural network 23A that outputs the fat mass as the estimation result relating to the composition of the soft tissue in a case in which the simple radiation image G0 is input.

In addition, in each of the embodiments described above, the estimation result relating to the composition of the soft tissue is derived from the simple radiation image G0, but the present disclosure is not limited to this. For example, also in a case in which the estimation result relating to the composition of the soft tissue is derived from the DXA scanning image acquired by imaging the subject with a DXA imaging apparatus disclosed in JP-H9-108206A (JP1997-108206A) and JP2006-271437A, the technology of the present disclosure can be applied. The DXA scanning image is the radiation image captured by the radiation detector by irradiating the subject while switching between a finely collimated high-energy radiation beam and a low-energy radiation beam and scanning The finely collimated radiation beam is, for example, a radiation beam formed into a pencil beam, a narrow fan beam, a wide fan beam, or the like by using a collimator positioned between the radiation source and the subject. The low-energy radiation refers to radiation with a relatively lower energy than the high-energy radiation.

In this case, according to each condition, such as the pixel size of the detector that images the DXA scanning image, the scanning direction and the scanning speed at the time of imaging, the distance between the X-ray source, the subject, and the detector, or the energy distribution of the radiation (determined by the tube voltage, the target, and the filter), the image simulating the DXA scanning image may be generated from the composite two-dimensional image C0, and the trained neural network 23A may be constructed by using the generated image simulating the DXA scanning image as the learning data 41.

The image simulating the DXA scanning image need only be generated by performing, for example, processing of reducing the resolution on the composite two-dimensional image C0 derived by the combining unit 68 in the fourth to sixth embodiments depending on the pixel size of the detector used for capturing the DXA scanning image, the scanning direction, the scanning speed, or the like. The image simulating the DXA scanning image is an example of a low-resolution composite two-dimensional image.

Specifically, the image simulating the DXA scanning image is generated as follows. A case will be assumed in which L, M, and N are natural numbers, and M×M pixels of the composite two-dimensional image C0 and N×N pixels of an image for learning of the DXA scanning image correspond to L mm×L mm of the actual size of the subject H. In this case, the resolution of the composite two-dimensional image C0 is reduced by setting the average value of the pixel values of (M/N)×(M/N) pixels of the composite two-dimensional image C0 to all pixel values of (M/N)×(M/N) pixels of the composite two-dimensional image C0 such that (M/N)×(M/N) pixels of the composite two-dimensional image C0, that is, a plurality of adjacent pixels correspond to one pixel of the image for learning of the DXA scanning image. Further, by performing such the resolution reduction processing in all the regions corresponding to the DXA scanning image of the composite two-dimensional image C0, the image simulating the DXA scanning image is generated. In a case in which the M/N is not a natural number, the positions of the corresponding pixels of the composite two-dimensional image C0 and the image for learning the DXA scanning image need only be appropriately adjusted by natural numbers before and behind the M/N to generate the image simulating the DXA scanning image from the composite two-dimensional image C0.

Further, as the resolution reduction processing for simulating blurriness due to scanning, the image simulating the DXA scanning image may be generated by performing the movement average processing in one direction corresponding to the scanning direction.

In addition, the image simulating the DXA scanning image may be generated by performing the movement average processing on the composite two-dimensional image C0. In the movement average processing, the size of the filter used for the calculation of the movement average and the intensity distribution of the filter need only be appropriately determined from the scanning direction and scanning speed at the time of imaging the DXA scanning image, the pixel size of the detector, the distance between the X-ray source, the subject, and the detector, and the like. For example, the resolution is lower as the scanning speed is faster, and thus the filter size need only be set relatively large. In this case, in a case in which L=10 is set, it is about M=200 and N=5.

Note that, in each of the embodiments described above, the predetermined part is the buttock, the lower limb, the limbs, and the like, but the present disclosure is not limited to this. In the present embodiment, it is possible to derive the estimation result relating to the composition of soft tissue for any part.

Figure 37:
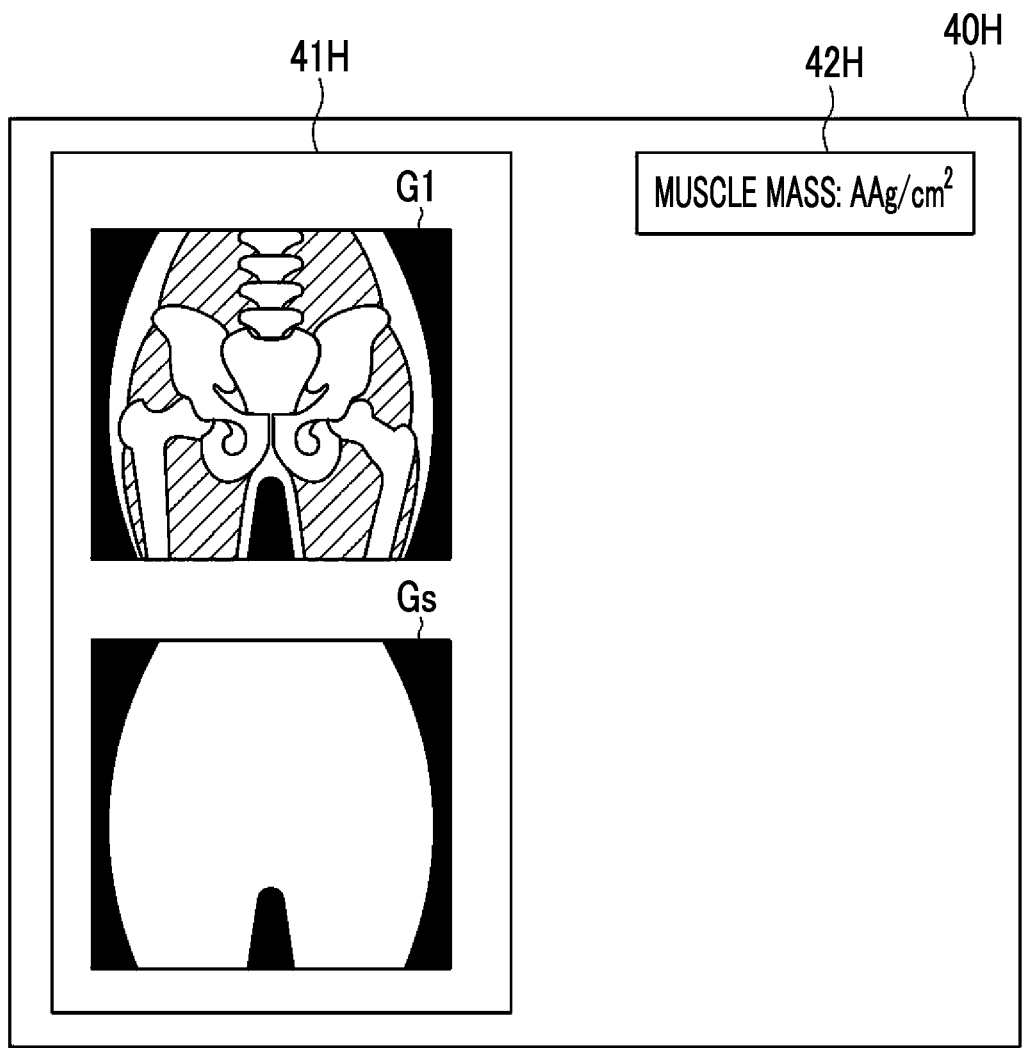
FIG. 37 is a diagram showing the teacher data using the soft part image as learning data.

In addition, in the first to third, and seventh embodiments described above, the first and second radiation images G1 and G2 are used as the learning data 41 of the teacher data 40, but the present disclosure is not limited to this. As shown in teacher data 40H of FIG. 37, the soft part image Gs derived by the subtraction unit 63 may be used as learning data 41H instead of the second radiation image G2. Note that, in FIG. 37, correct answer data 42H is the muscle mass.

In addition, in each of the first to third, and seventh embodiments described above, the first radiation image G1 and the second radiation image G2 itself are used in a case in which the muscle mass as the correct answer data is derived, but the present disclosure is not limited to this. For each pixel of the first radiation image G1 and the second radiation image G2, a movement average with the surrounding pixels is calculated, and the first radiation image G1 and the second radiation image G2 in which the movement average is used as the pixel value of each pixel may be used to derive the muscle mass. In this case, the pixels to be used as the movement average need only be appropriately determined from information on a mutual distance between the radiation source 3, the subject H, and the radiation detectors 5 and 6, information on a pixel size of the radiation detectors 5 and 6, and the like.

Note that, in each of the embodiments described above, the estimation device 10 trains the neural network to construct the trained neural network 23A, but the present disclosure is not limited to this. The trained neural network 23A constructed in a device other than the estimation device 10 may be used for the estimation unit 23 of the estimation device 10 in the present embodiment.

In addition, in each of the first to third, and seventh embodiments described above, the first and second radiation images G1 and G2 are acquired by the one-shot method in a case in which the energy subtraction processing is performed for deriving the muscle mass, but the present disclosure is not limited to this. The first and second radiation images G1 and G2 may be acquired by a so-called two-shot method in which imaging is performed twice by using only one radiation detector. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed.

As registration processing, for example, a method disclosed in JP2011-255060A can be used. In the method disclosed in JP2011-255060A, for each of the first and second radiation images G1 and G2, a plurality of first band images and a plurality of second band images representing structures having different frequency bands are generated, a misregistration amount of the positions corresponding to each other in the first band image and the second band image of the corresponding frequency band is acquired, and the registration of the first radiation image G1 and the second radiation image G2 is performed based on the misregistration amount.

In addition, in each of the embodiments described above, the information relating to the composition of the soft tissue as the correct answer data of the teacher data is performed by using the radiation image acquired by the system that images the subject H by using the first and second radiation detectors 5 and 6, but the information relating to the composition of the soft tissue as the correct answer data may be derived from the first and second radiation images G1 and G2 acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation in the embodiments described above is not particularly limited, and α-rays or γ-rays can be used in addition to X-rays.

In addition, in the embodiments described above, various processors shown below can be used as the hardware structures of processing units that execute various pieces of processing, such as the image acquisition unit 21, the information acquisition unit 22, the estimation unit 23, the learning unit 24, and the display controller 25 of the estimation device 10, and the image acquisition unit 61, the scattered ray removal unit 62, the subtraction unit 63, and the muscle mass derivation unit 64 of the information derivation device 50. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. An estimation device comprising:
at least one processor,
wherein the processor functions as a trained neural network that derives an estimation result relating to a composition of a soft tissue of a subject from a simple radiation image acquired by simply imaging the subject, or a DXA scanning image acquired by imaging the subject by a DXA method, and
the trained neural network learns using, as teacher data, (i) two radiation images acquired by imaging the subject with radiation having different energy distributions, (ii) the radiation image of the subject and a soft part image representing the soft tissue of the subject, or (iii) a composite two-dimensional image representing the subject derived by combining a three-dimensional CT image of the subject, and information relating to the composition of the soft tissue of the subject.

2. The estimation device according to claim 1,
wherein the information relating to the composition of the soft tissue is derived based on a pixel value of a soft region of a soft part image derived from the two radiation images acquired by imaging the subject with the radiation having different energy distributions.

3. The estimation device according to claim 1,
wherein the information relating to the composition of the soft tissue is obtained by specifying a soft region in the CT image, deriving an attenuation coefficient of radiation in the soft region, and deriving the information relating to the composition of the soft tissue based on a density of the composition of the soft tissue, which is derived based on the attenuation coefficient of the radiation and a mass attenuation coefficient in the soft region.

4. The estimation device according to claim 3,
wherein the information relating to the composition of the soft tissue is derived by projecting the density of the composition at each position in the soft region in a predetermined direction.

5. The estimation device according to claim 1,
wherein the information relating to the composition of the soft tissue includes at least one of a muscle mass per unit area, a muscle mass per unit volume, a fat mass per unit area, a fat mass per unit volume, disease information representing an affection risk of a predetermined disease or a disease level of the predetermined disease, or a falling-down rate.

6. The estimation device according to claim 5,
wherein the disease information is derived by deriving the muscle mass of a predetermined part of the subject, and specifying the disease information based on correspondence relationship information representing a correspondence relationship between the disease information representing the affection risk of the predetermined disease or the disease level of the predetermined disease and the muscle mass of the predetermined part, and the muscle mass.

7. The estimation device according to claim 5,
wherein the disease information is derived by deriving the muscle mass and a bone mineral density of a predetermined part of the subject, and specifying the disease information based on correspondence relationship information representing a correspondence relationship between the disease information representing the affection risk of the predetermined disease or the disease level of the predetermined disease and the muscle mass of the predetermined part, the muscle mass, and the bone mineral density.

8. The estimation device according to claim 6,
wherein the predetermined part is a lower limb,
the predetermined disease is diabetes, and
the disease information is the affection risk of the diabetes.

9. The estimation device according to claim 6,
wherein the predetermined part is limbs or a whole body,
the predetermined disease is sarcopenia, and
the disease information is the disease level of the sarcopenia.

10. The estimation device according to claim 5,
wherein the falling-down rate is derived by deriving the muscle mass of a predetermined part of the subject, and specifying the falling-down rate based on correspondence relationship information representing a correspondence relationship between muscle information, which is the muscle mass of the predetermined part or a muscle strength in accordance with the muscle mass of the predetermined part, and the falling-down rate of the subject, and the muscle mass.

11. The estimation device according to claim 5,
wherein the falling-down rate is derived by deriving the muscle mass and a bone mineral density of a predetermined part of the subject, and specifying the falling-down rate based on correspondence relationship information representing a correspondence relationship between muscle information, which is the muscle mass of the predetermined part or a muscle strength in accordance with the muscle mass of the predetermined part, and the falling-down rate of the subject, the muscle mass, and the bone mineral density.

12. The estimation device according to claim 10,
wherein the predetermined part is at least one of a lower limb or a buttock.

13. The estimation device according to claim 1,
wherein the processor functions as the trained neural network that derives the estimation result relating to the composition of the soft tissue from the DXA scanning image, and
the trained neural network learns using, as the teacher data, a low-resolution composite two-dimensional image obtained by performing processing of reducing a resolution on the composite two-dimensional image, and the information relating to the composition of the soft tissue of the subject.

14. The estimation device according to claim 13,
wherein the low-resolution composite two-dimensional image is an image in which an average value of pixel values of a plurality of adjacent pixels of the composite two-dimensional image is used as the pixel values of the plurality of adjacent pixels, and
sizes of the plurality of adjacent pixels correspond to one pixel size of the DXA scanning image.

15. The estimation device according to claim 13,
wherein the low-resolution composite two-dimensional image is an image obtained by performing movement average processing on the composite two-dimensional image in one direction, and
the one direction corresponds to a scanning direction of the DXA scanning image.

16. The estimation device according to claim 13,
wherein the low-resolution composite two-dimensional image is an image generated by generating a first low-resolution image in which an average value of pixel values of a plurality of adjacent pixels of the composite two-dimensional image is used as the pixel values of the plurality of adjacent pixels, and performing movement average processing on the first low-resolution image in one direction,
sizes of the plurality of adjacent pixels correspond to one pixel size of the DXA scanning image, and
the one direction corresponds to a scanning direction of the DXA scanning image.

17. An estimation method comprising:
using a trained neural network that derives an estimation result relating to a composition of a soft tissue of a subject from a simple radiation image acquired by simply imaging the subject, or a DXA scanning image acquired by imaging the subject by a DXA method to derive the estimation result relating to the composition of the soft tissue from the simple radiation image or the DXA scanning image,
wherein the trained neural network learns using, as teacher data, (i) two radiation images acquired by imaging the subject with radiation having different energy distributions, (ii) the radiation image of the subject and a soft part image representing the soft tissue of the subject, or (iii) a composite two-dimensional image representing the subject derived by combining a three-dimensional CT image of the subject, and information relating to the composition of the soft tissue of the subject.

18. A non-transitory computer-readable storage medium that stores an estimation program causing a computer to execute a procedure of:
using a trained neural network that derives an estimation result relating to a composition of a soft tissue of a subject from a simple radiation image acquired by simply imaging the subject, or a DXA scanning image acquired by imaging the subject by a DXA method to derive the estimation result relating to the composition of the soft tissue from the simple radiation image or the DXA scanning image,
wherein the trained neural network learns using, as teacher data, (i) two radiation images acquired by imaging the subject with radiation having different energy distributions, (ii) the radiation image of the subject and a soft part image representing the soft tissue of the subject, or (iii) a composite two-dimensional image representing the subject derived by combining a three-dimensional CT image of the subject, and information relating to the composition of the soft tissue of the subject.

* * * * *